US007292329B2

(12) United States Patent
Treves et al.

(10) Patent No.: US 7,292,329 B2
(45) Date of Patent: Nov. 6, 2007

(54) TEST HEAD FOR OPTICALLY INSPECTING WORKPIECES COMPRISING A LENS FOR ELONGATING A LASER SPOT ON THE WORKPIECES

(75) Inventors: David Treves, Palo Alto, CA (US); Thomas A. O'Dell, Campbell, CA (US)

(73) Assignee: Komag, Inc., San Jose, CA (US)

( * ) Notice: Subject to any disclaimer, the term of this patent is extended or adjusted under 35 U.S.C. 154(b) by 31 days.

(21) Appl. No.: 11/113,261

(22) Filed: Apr. 23, 2005

(65) Prior Publication Data
US 2006/0152715 A1 Jul. 13, 2006

Related U.S. Application Data

(60) Provisional application No. 60/643,748, filed on Jan. 13, 2005.

(51) Int. Cl.
*G01N 21/00* (2006.01)
(52) U.S. Cl. .................................................. 356/237.2
(58) Field of Classification Search ... 356/237.2–237.5
See application file for complete search history.

(56) References Cited

U.S. PATENT DOCUMENTS

| | | | | |
|---|---|---|---|---|
| 3,917,414 A | * | 11/1975 | Geis et al. | 356/431 |
| 4,794,264 A | | 12/1988 | Quackenbos et al. | 250/563 |
| 4,794,265 A | | 12/1988 | Quackenbos et al. | 250/572 |
| 4,978,861 A | | 12/1990 | Sabater et al. | 250/571 |
| 5,164,603 A | * | 11/1992 | Hartman et al. | 250/559.46 |
| 5,339,300 A | * | 8/1994 | Akatsuka et al. | 369/44.29 |
| 5,471,298 A | * | 11/1995 | Moriya | 356/336 |
| 5,719,840 A | | 2/1998 | Jann | 369/58 |
| 5,875,029 A | | 2/1999 | Jann et al. | 356/345 |
| 6,292,259 B1 | * | 9/2001 | Fossey et al. | 356/237.2 |
| 6,515,745 B2 | * | 2/2003 | Vurens et al. | 356/369 |
| 6,548,821 B1 | | 4/2003 | Treves et al. | 250/559.45 |
| 6,566,674 B1 | | 5/2003 | Treves et al. | 250/559.46 |
| 6,678,043 B1 | * | 1/2004 | Vurens et al. | 356/237.2 |
| 6,829,047 B2 | | 12/2004 | Fujii et al. | 356/237.4 |

OTHER PUBLICATIONS

U.S. Appl. No. 11/113,258, entitled "Test Head for Optically Inspecting Workpieces", filed Apr. 23, 2005.
U.S. Appl. No. 11/113,260, entitled "Method and Apparatus for Selectively Providing Data from a Test Head to a Processor", filed Apr. 23, 2005.
U.S. Appl. No. 11/112,172, entitled "Test Head for Optically Inspecting Workpieces", filed Apr. 22, 2005.

(Continued)

*Primary Examiner*—Tarifur Chowdhury
*Assistant Examiner*—Isiaka O Akanbi

(57) ABSTRACT

An optical test head comprises a laser source for providing a laser beam. The laser beam passes through a cylindrical lens for modifying the shape of the beam and a spherical lens for concentrating the beam onto a workpiece (typically a magnetic disk platter). The cylindrical lens both a) elongates the laser beam along the radial direction of the platter (by reducing the effective numerical aperture in the radial direction); and b) causes the beam to be out of focus in the radial direction (although the beam is typically in focus in the circumferential direction). The size of the beam in the radial direction is substantially insensitive to the position of the cylindrical lens.

18 Claims, 19 Drawing Sheets

OTHER PUBLICATIONS

U.S. Appl. No. 11/112,190, entitled "Robotic System for Optically Inspecting Workpieces", filed Apr. 22, 2005.

U.S. Appl. No. 11/112,044, entitled "Method and Apparatus for Reducing or Eliminating Stray Light in an Optical Test Head", filed Apr. 22, 2005.

U.S. Appl. No. 11/112,536, entitled "Test Head for Optically Inspecting Workpieces", filed Apr. 22, 2005.

U.S. Appl. No. 11/112,909, entitled "Circularly Polarized Light for Optically Inspecting Workpeices", filed Apr. 22, 2005.

* cited by examiner

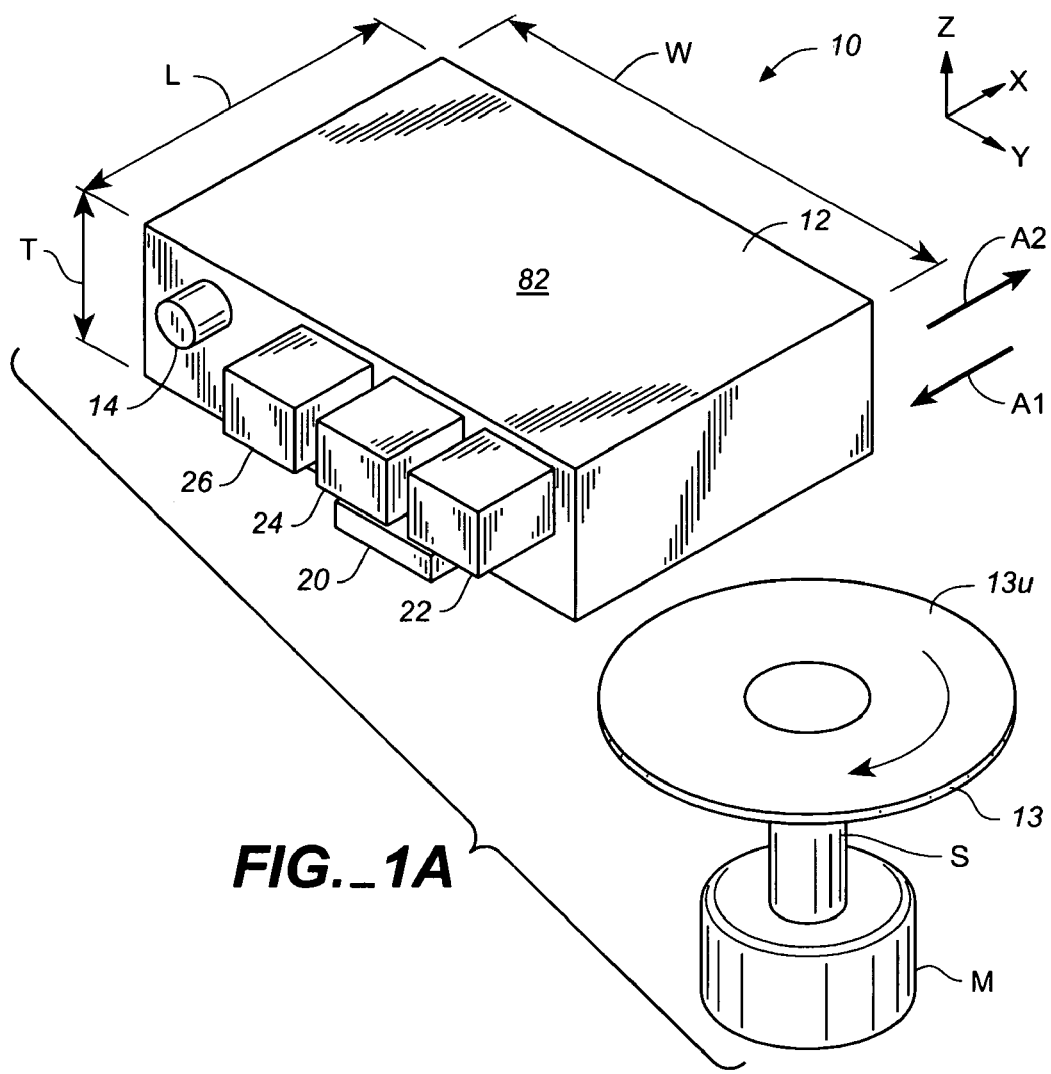
FIG._1A
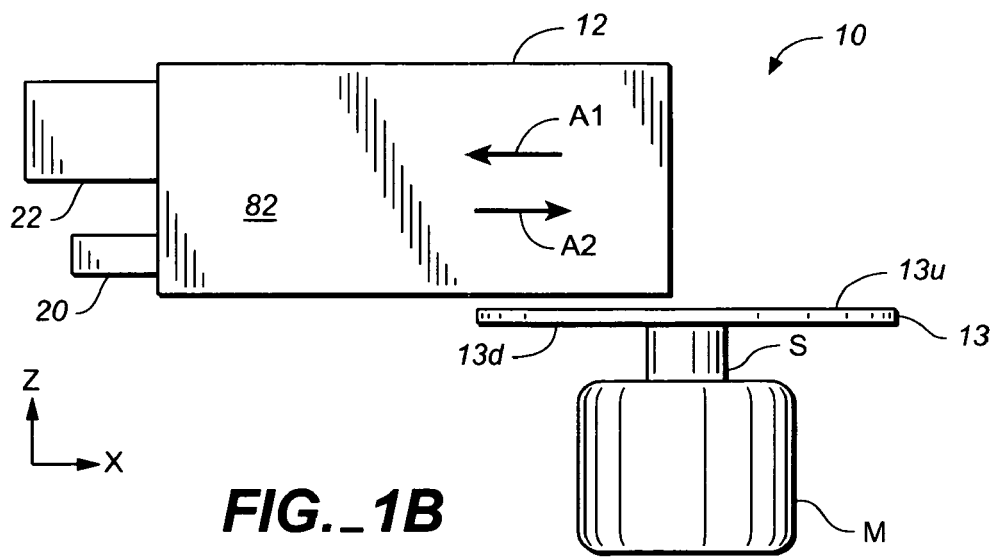
FIG._1B

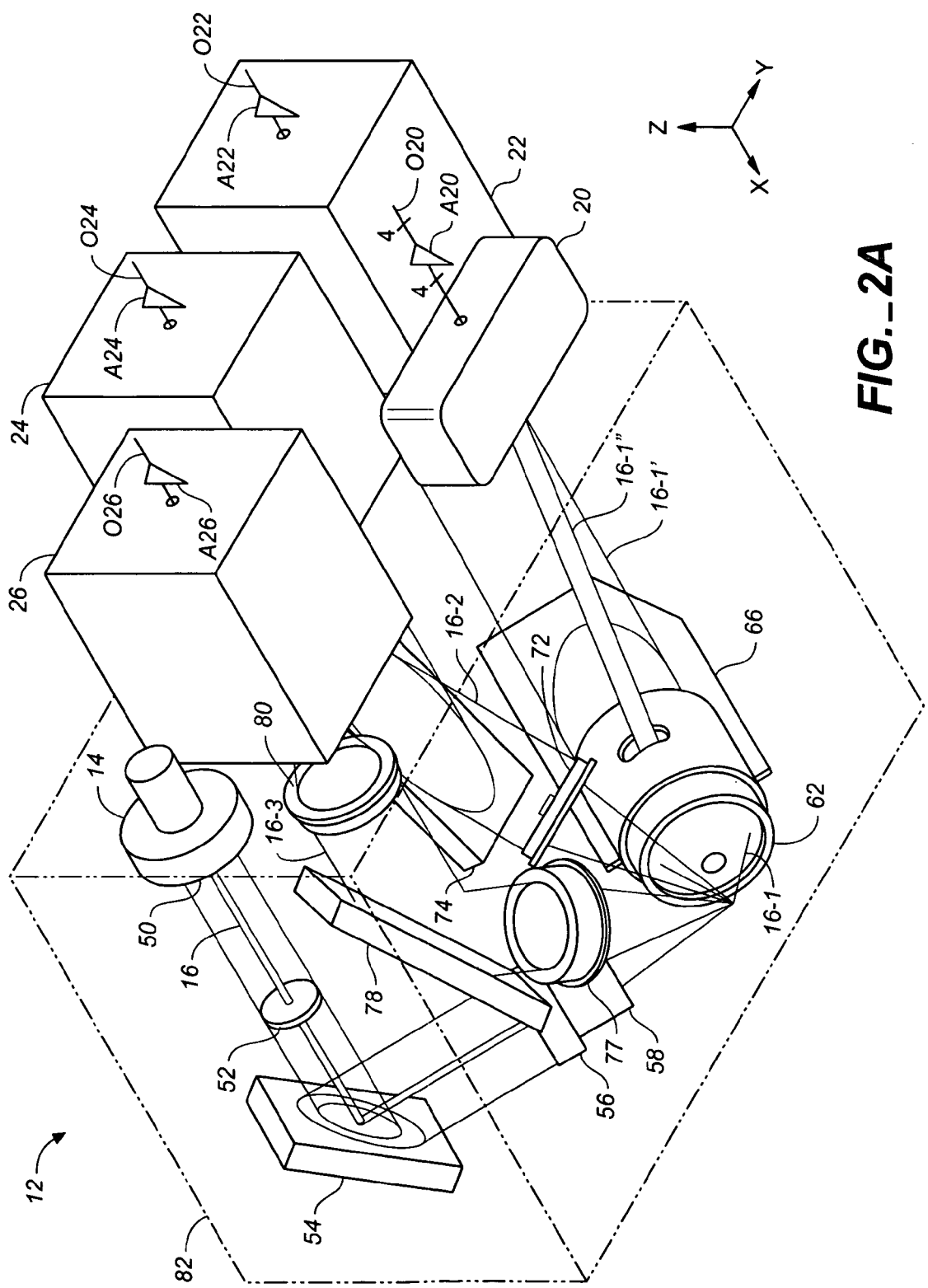
FIG._2A

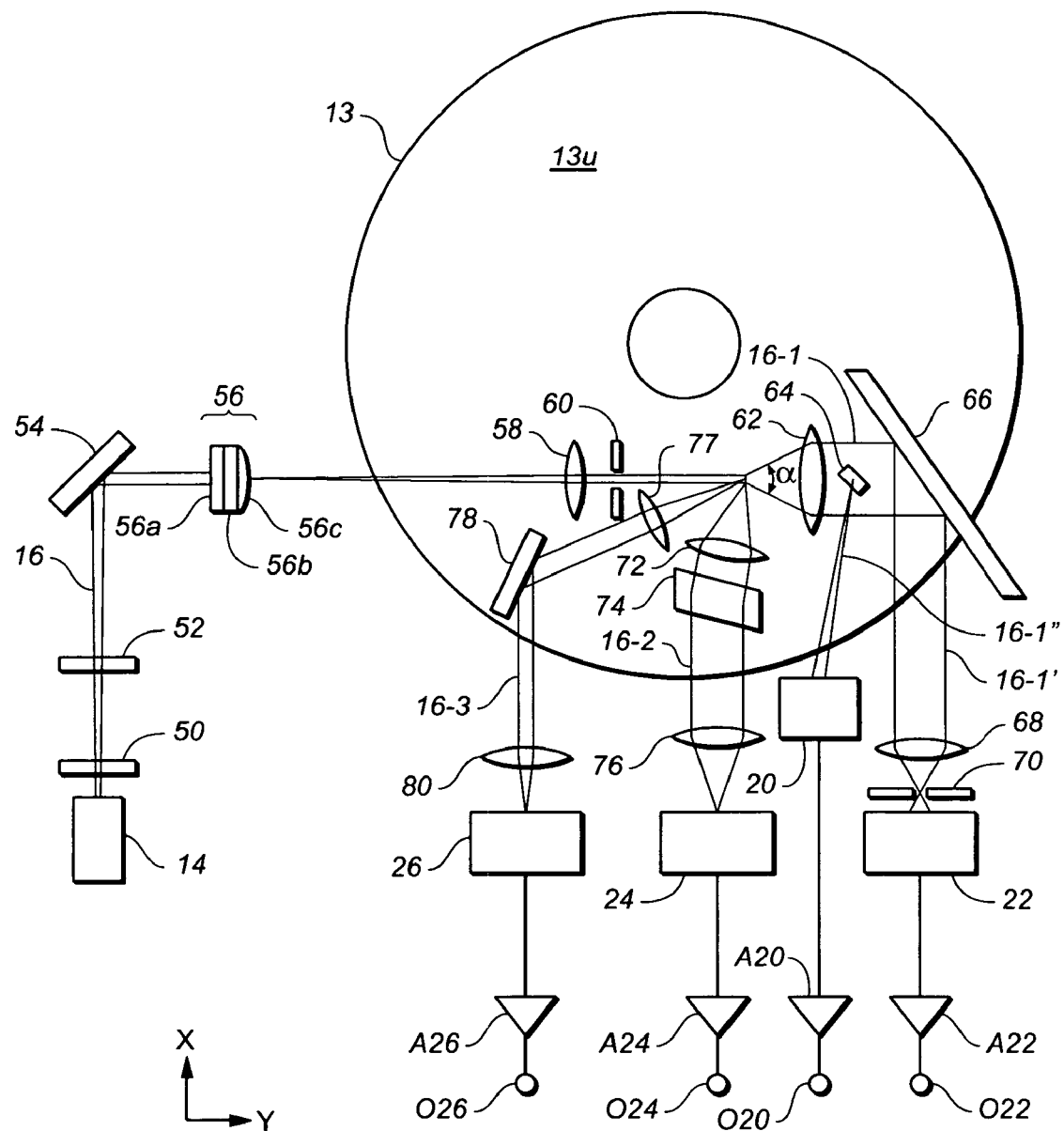
FIG._2B

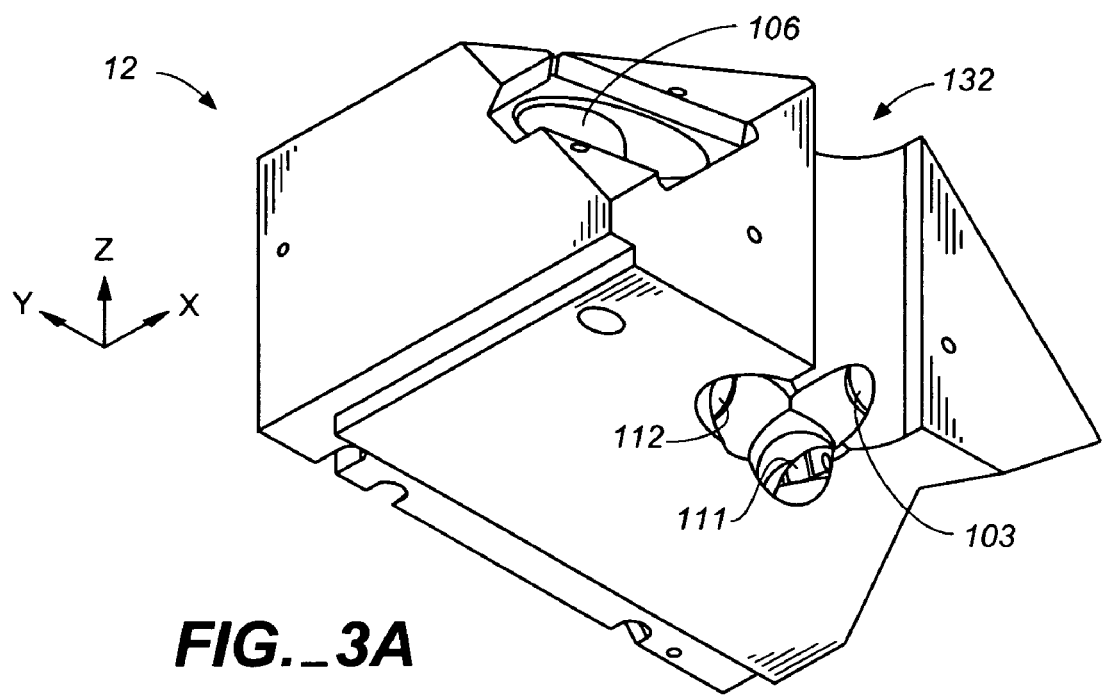
FIG._3A
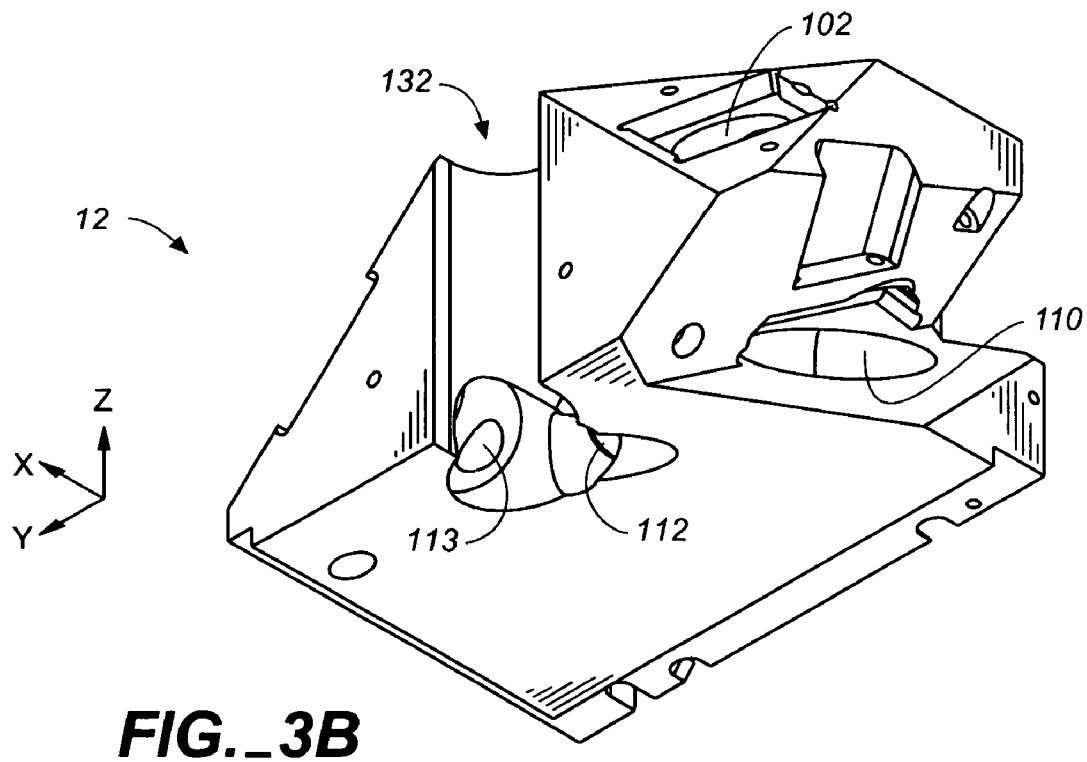
FIG._3B

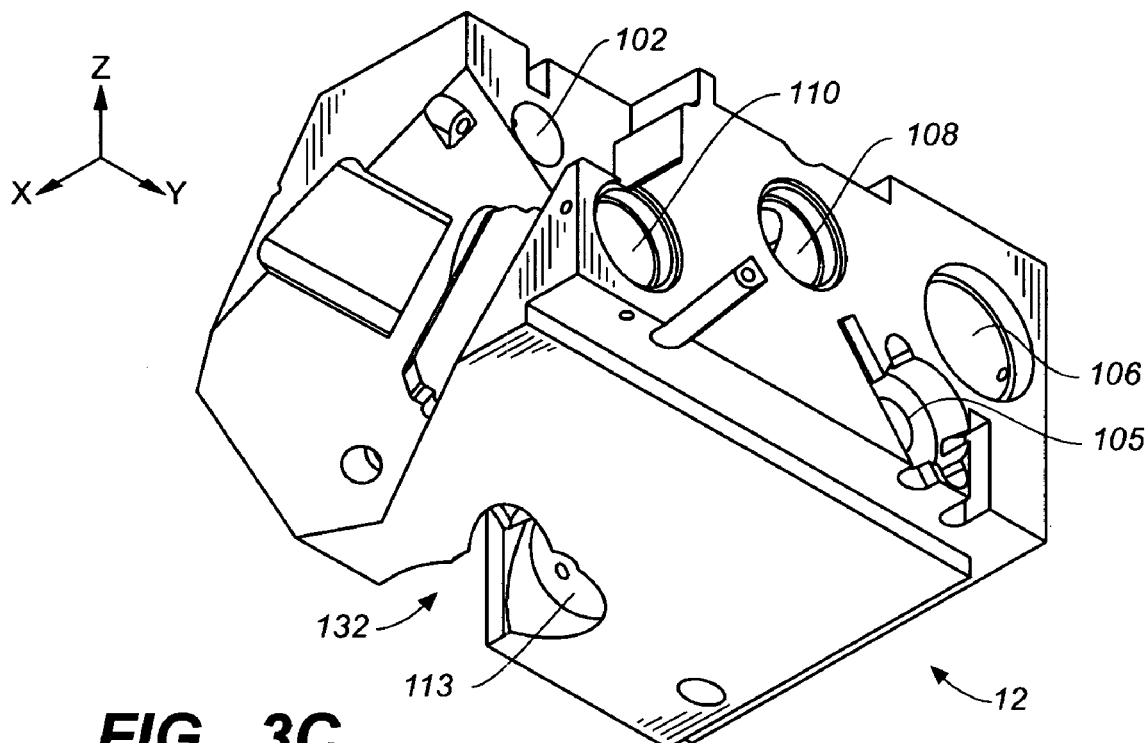
FIG._3C
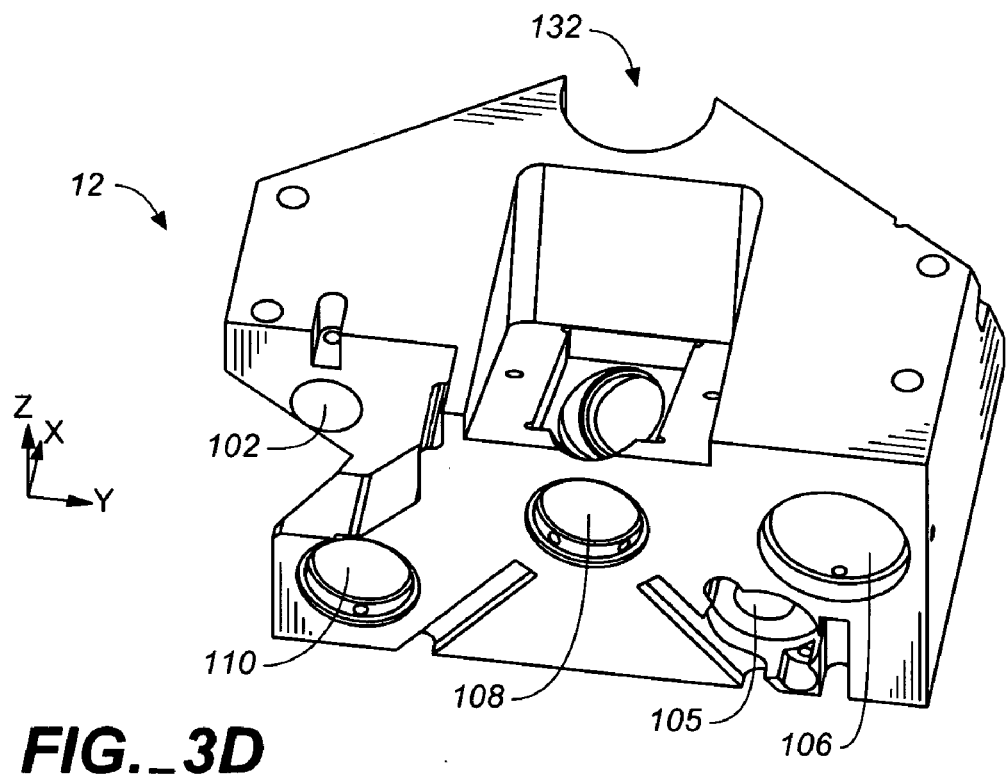
FIG._3D

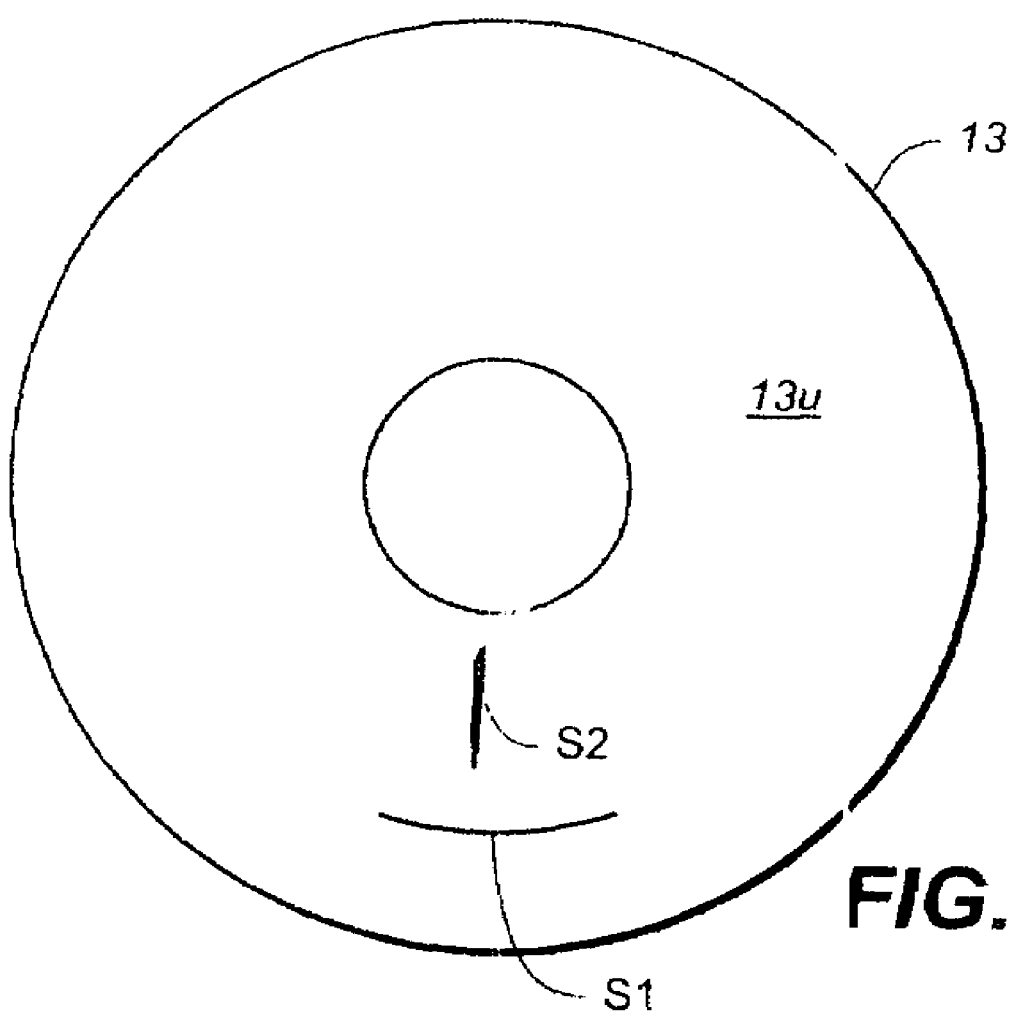
FIG._4

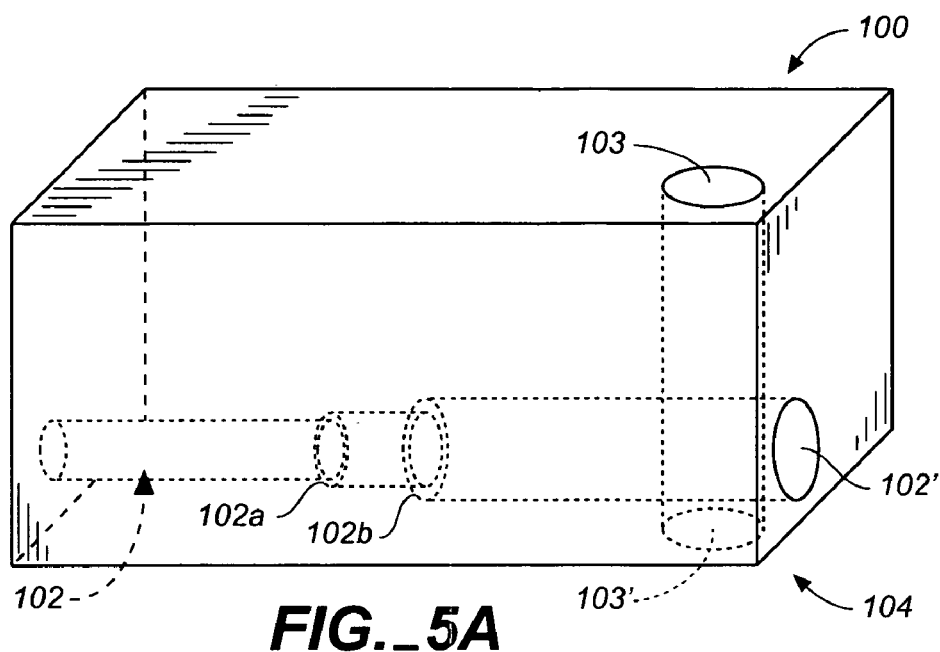
*FIG._5A*
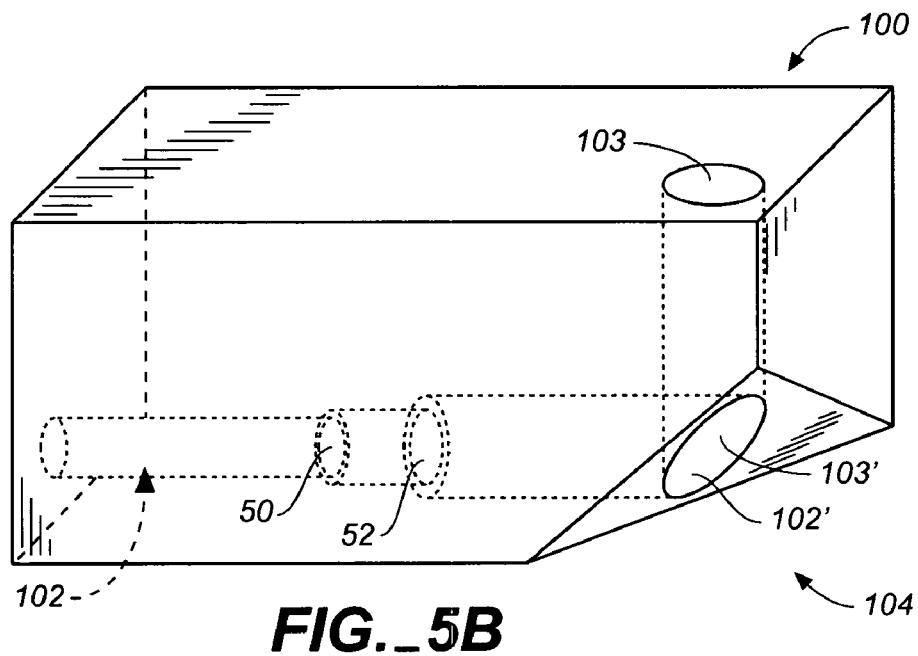
*FIG._5B*
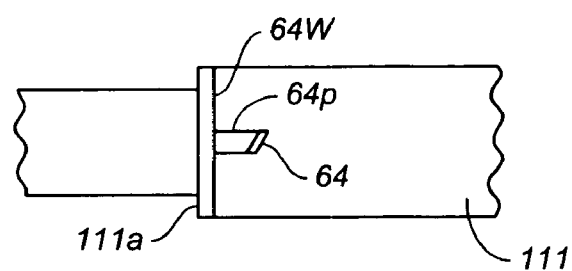
*FIG._5C*

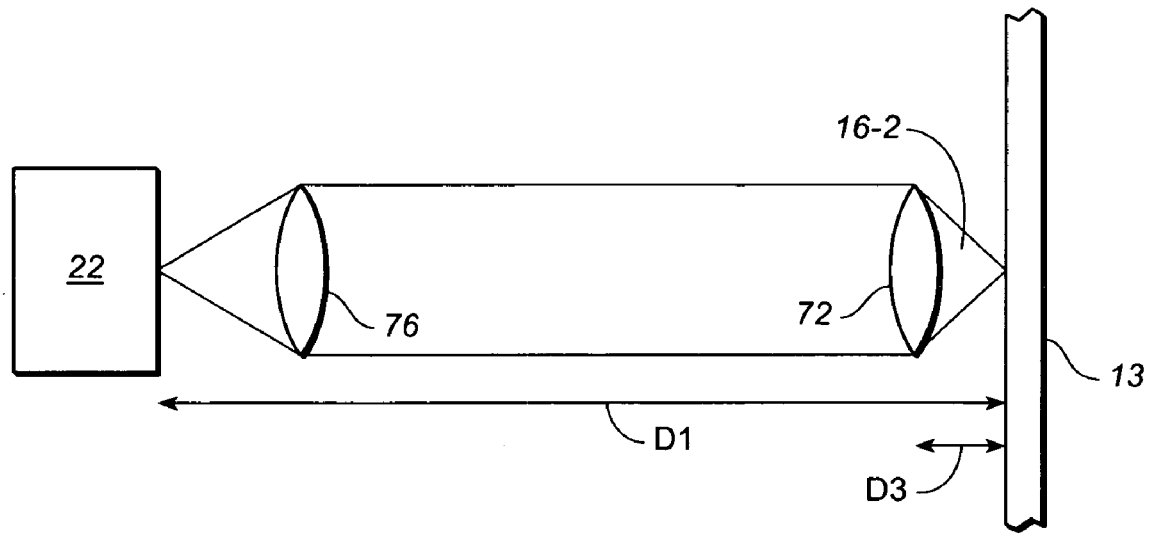
FIG._6A
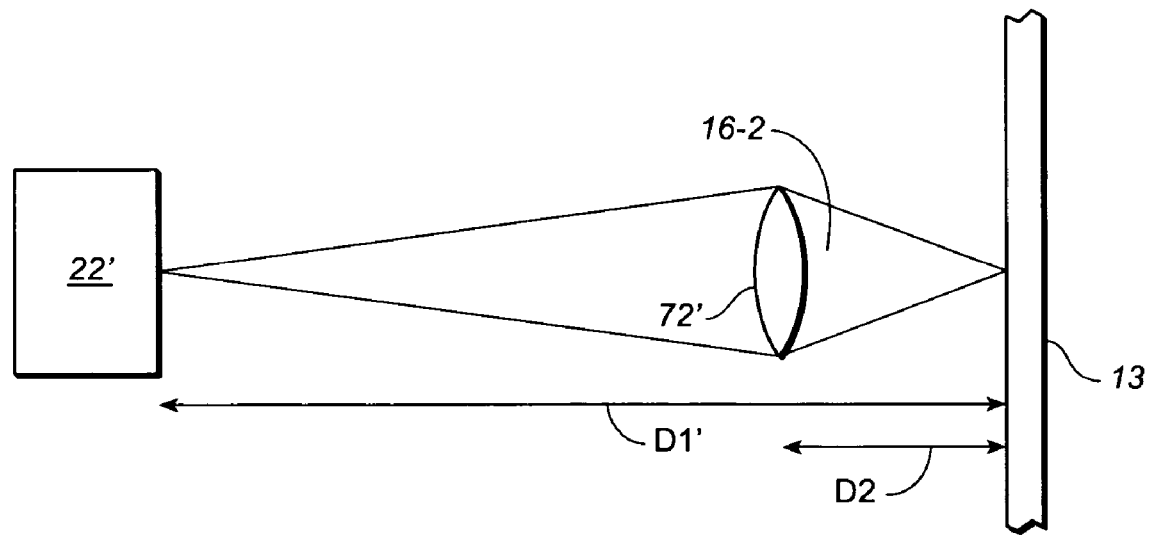
FIG._6B

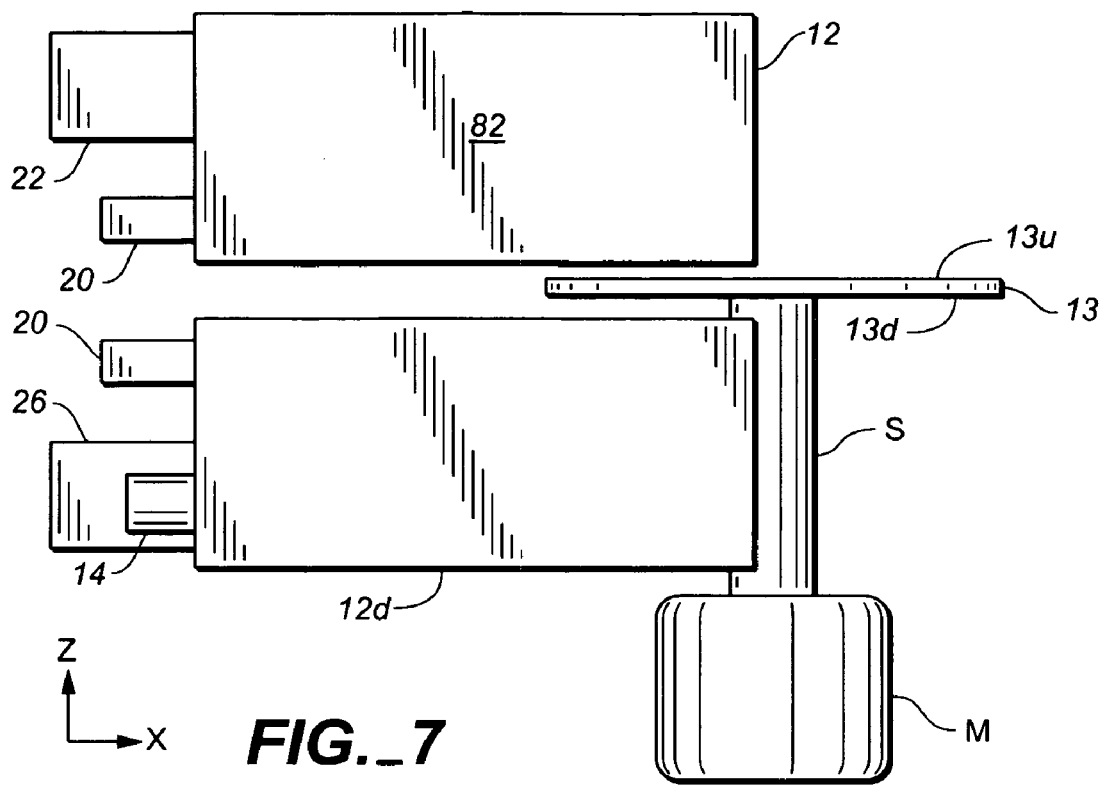
FIG._7
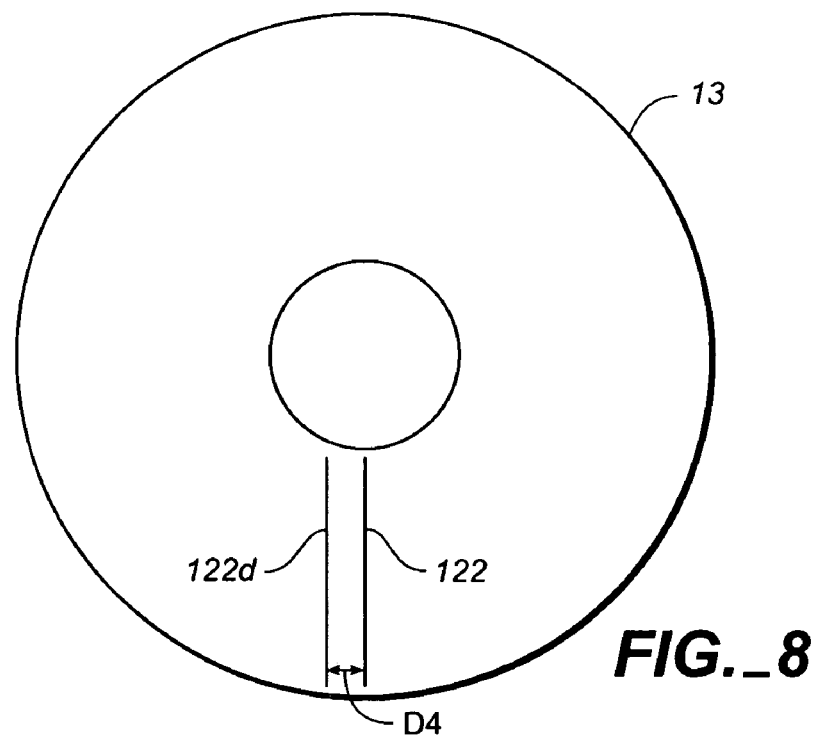
FIG._8

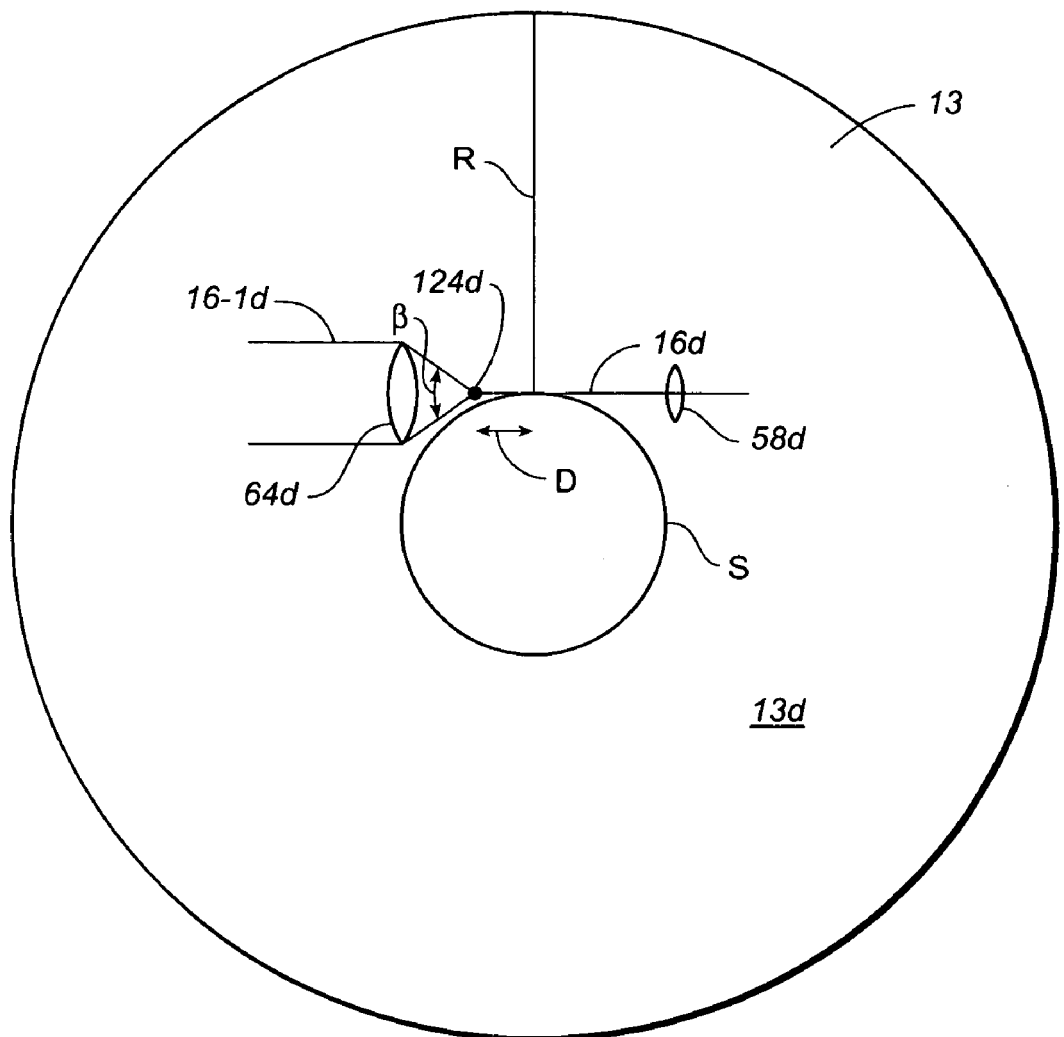
FIG._9
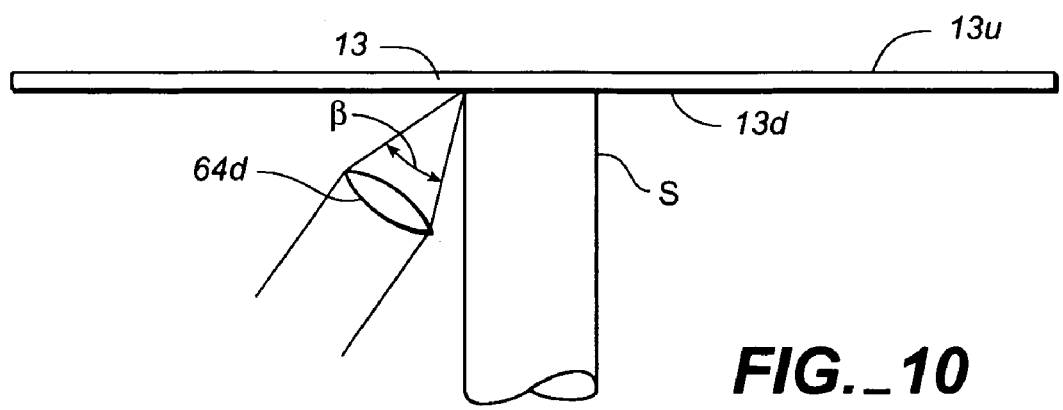
FIG._10

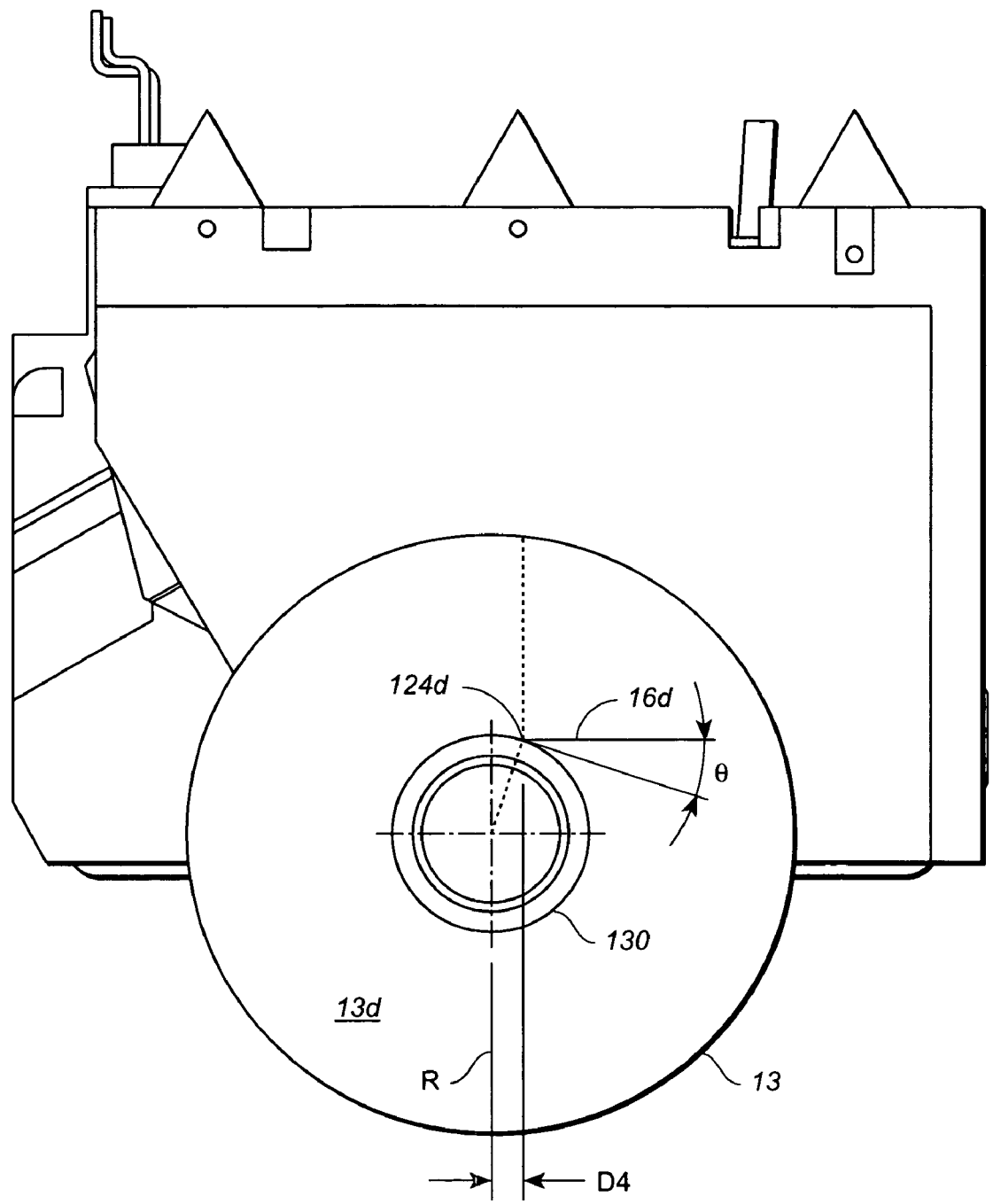
FIG._11

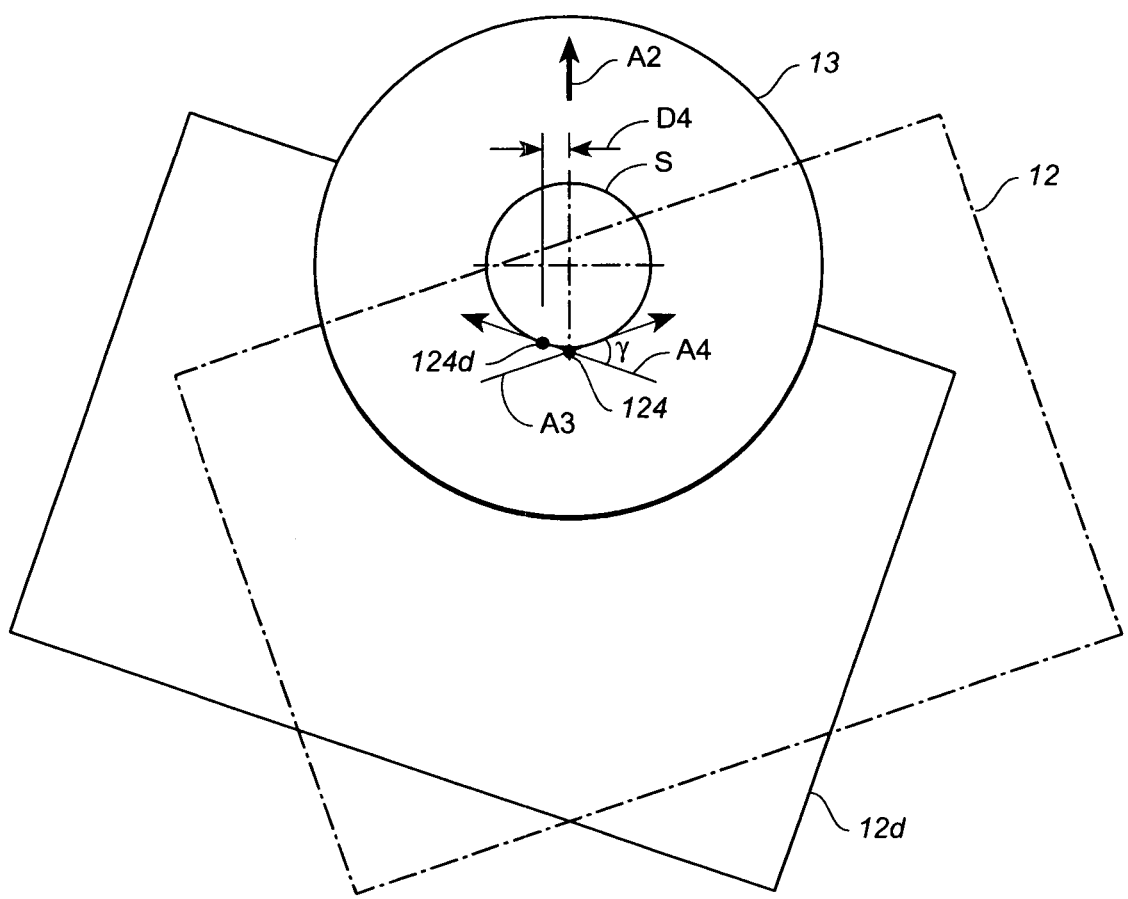
FIG._12

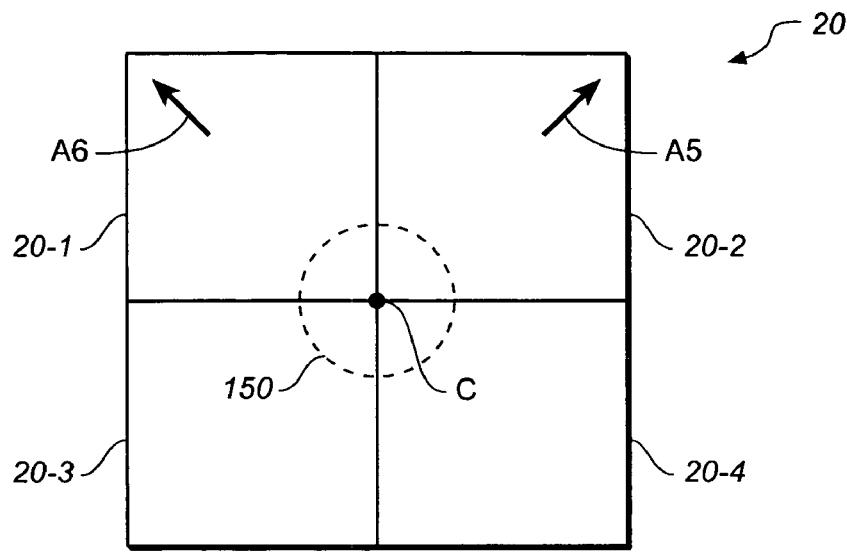
FIG._13
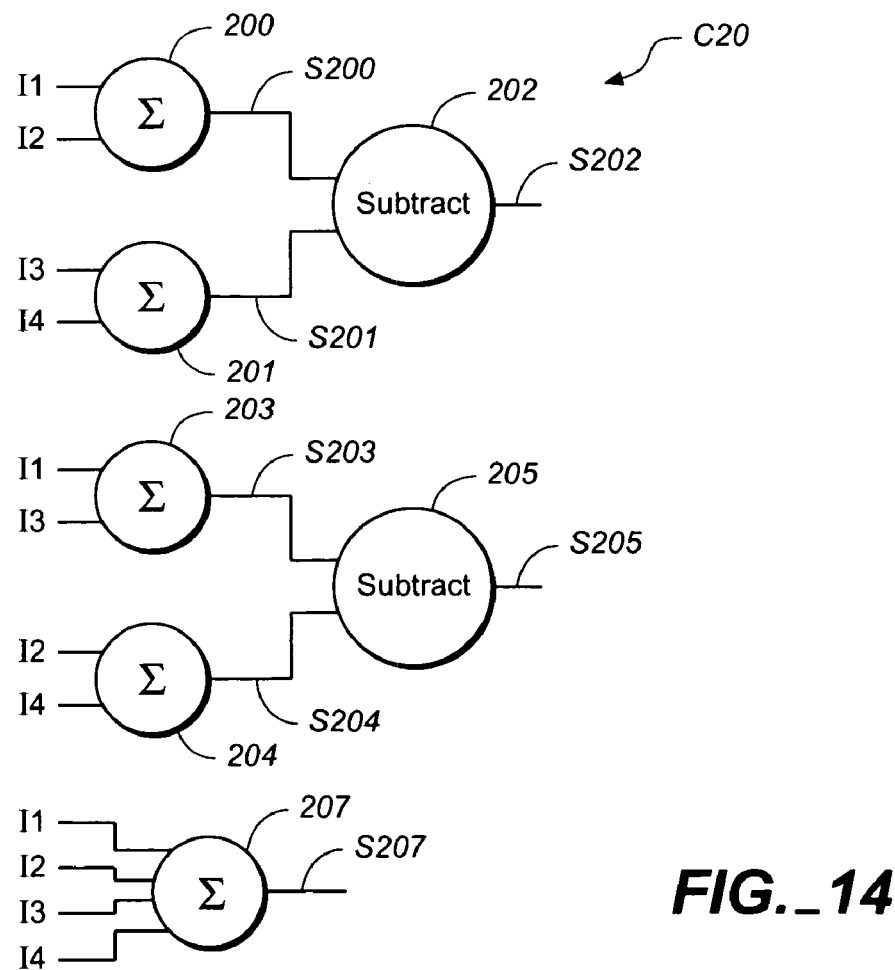
FIG._14

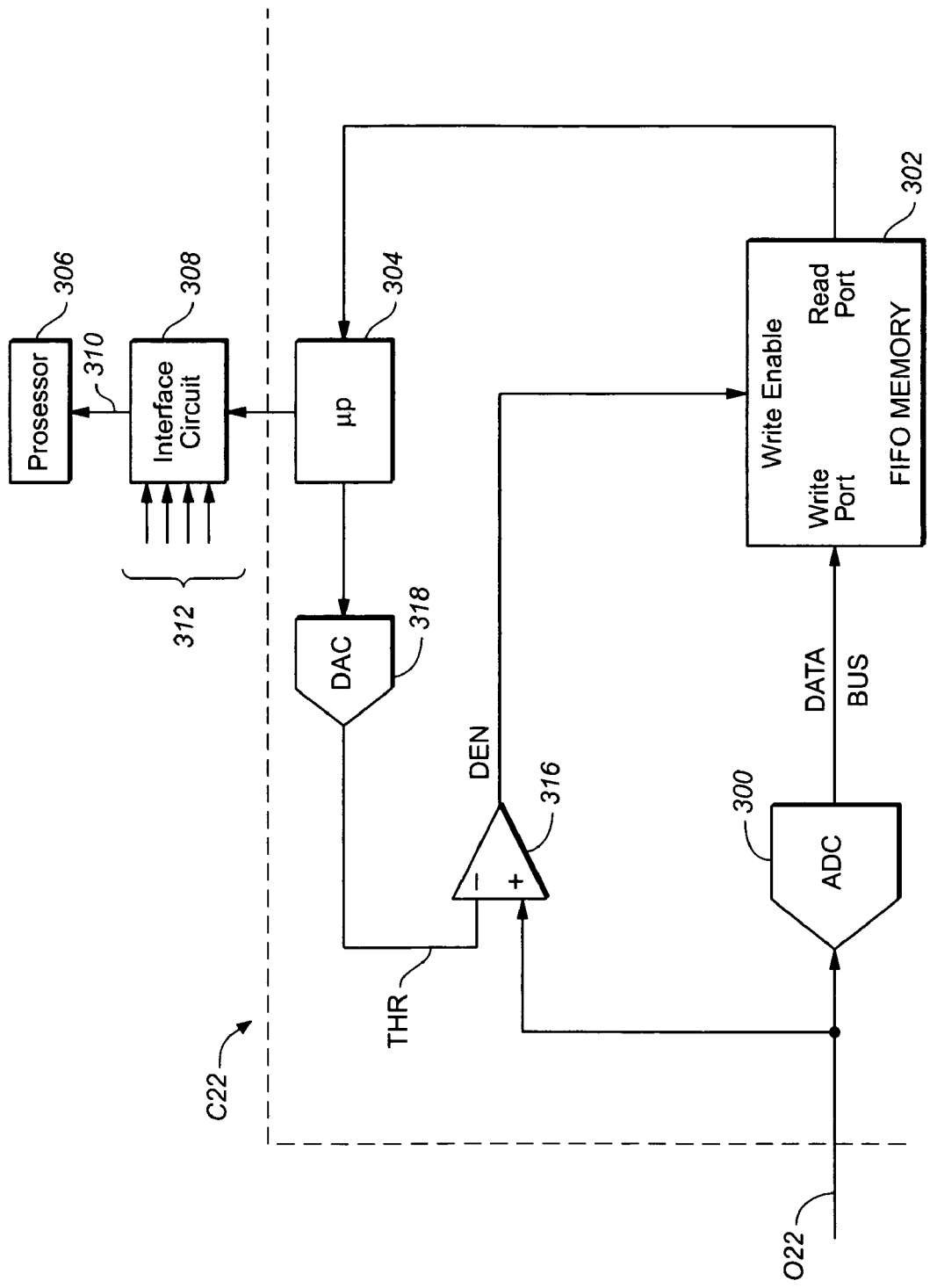
FIG._15A

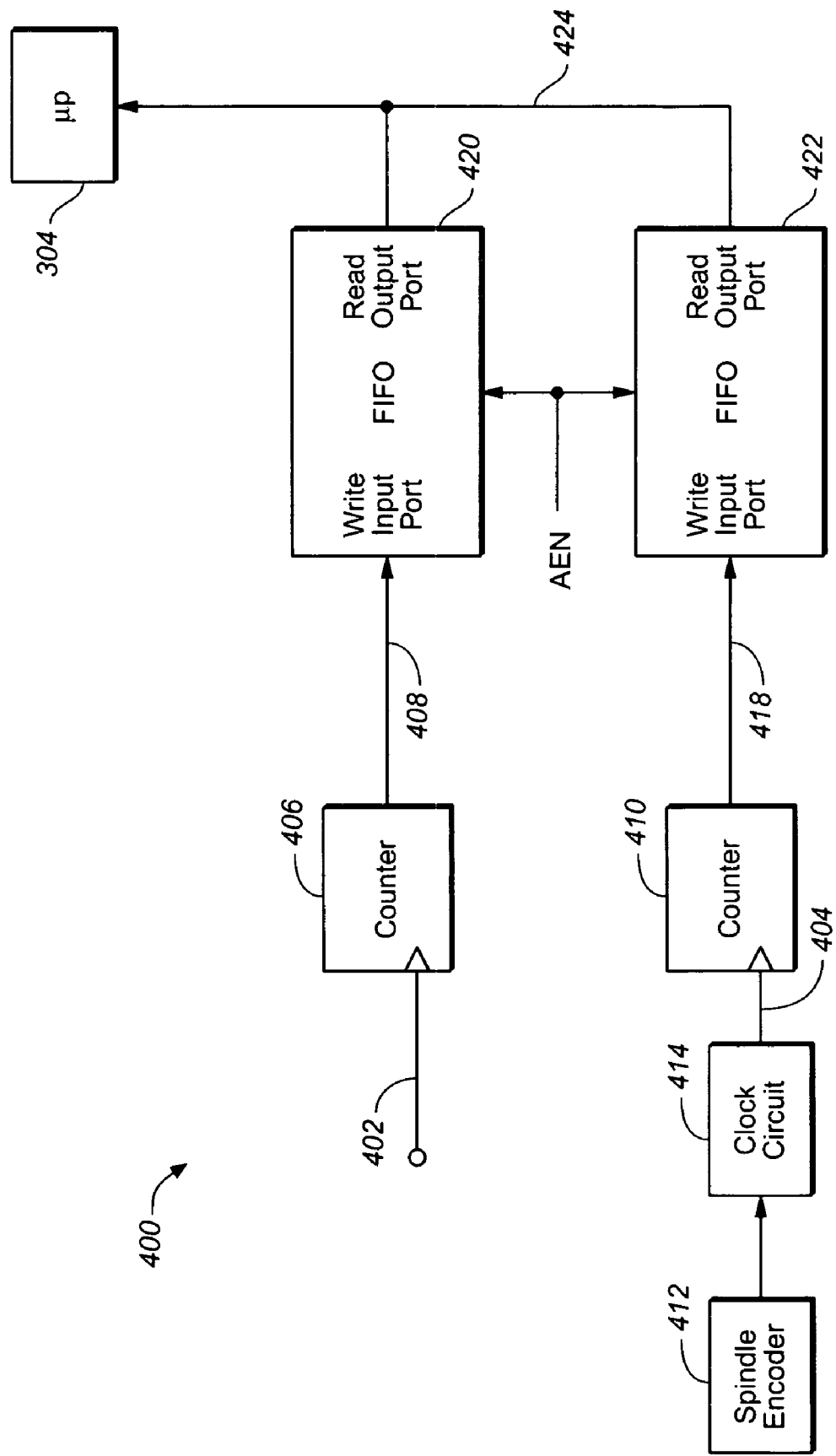
FIG._15B

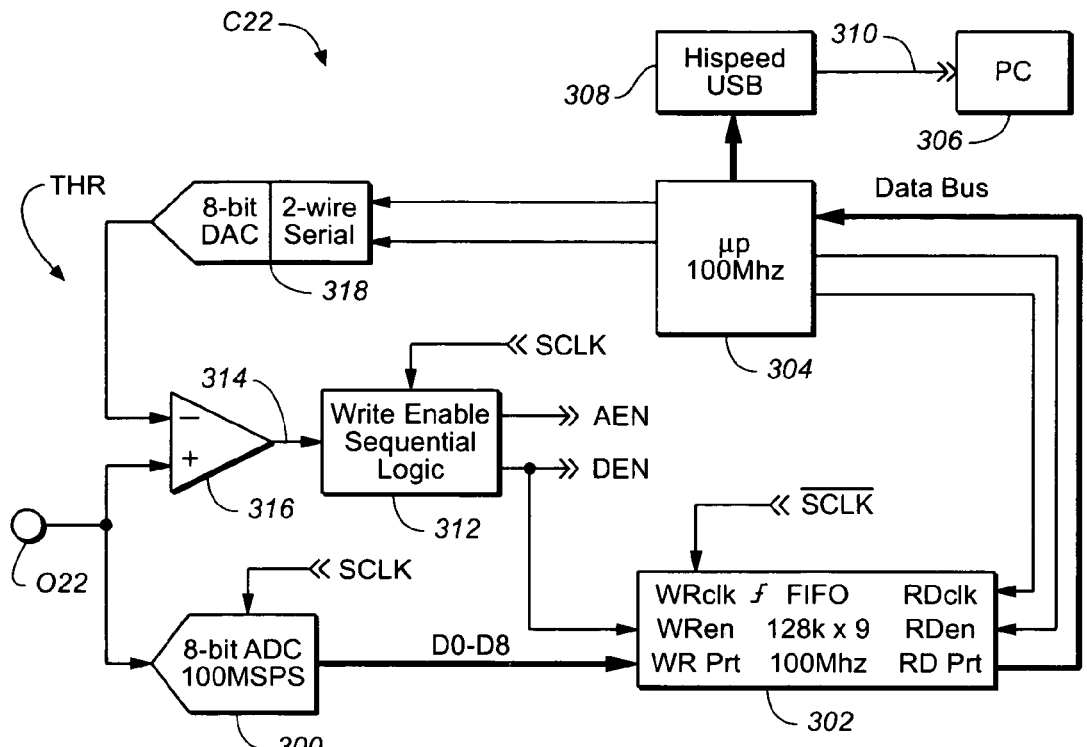
*FIG._16A*
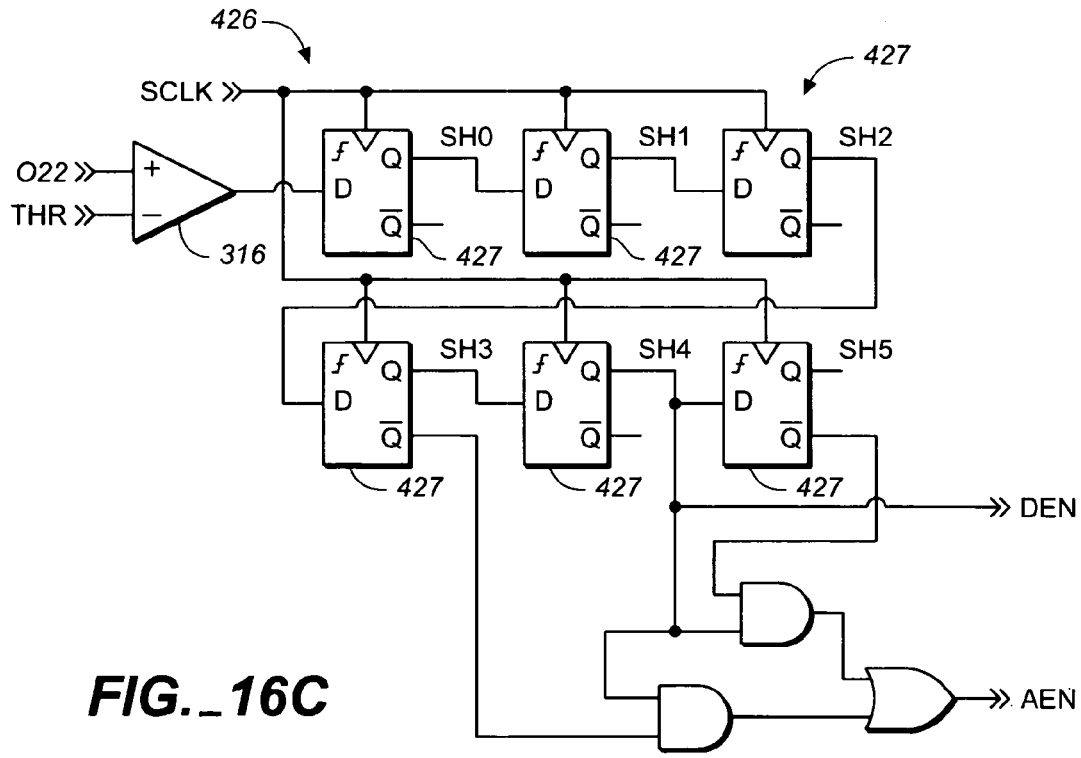
*FIG._16C*

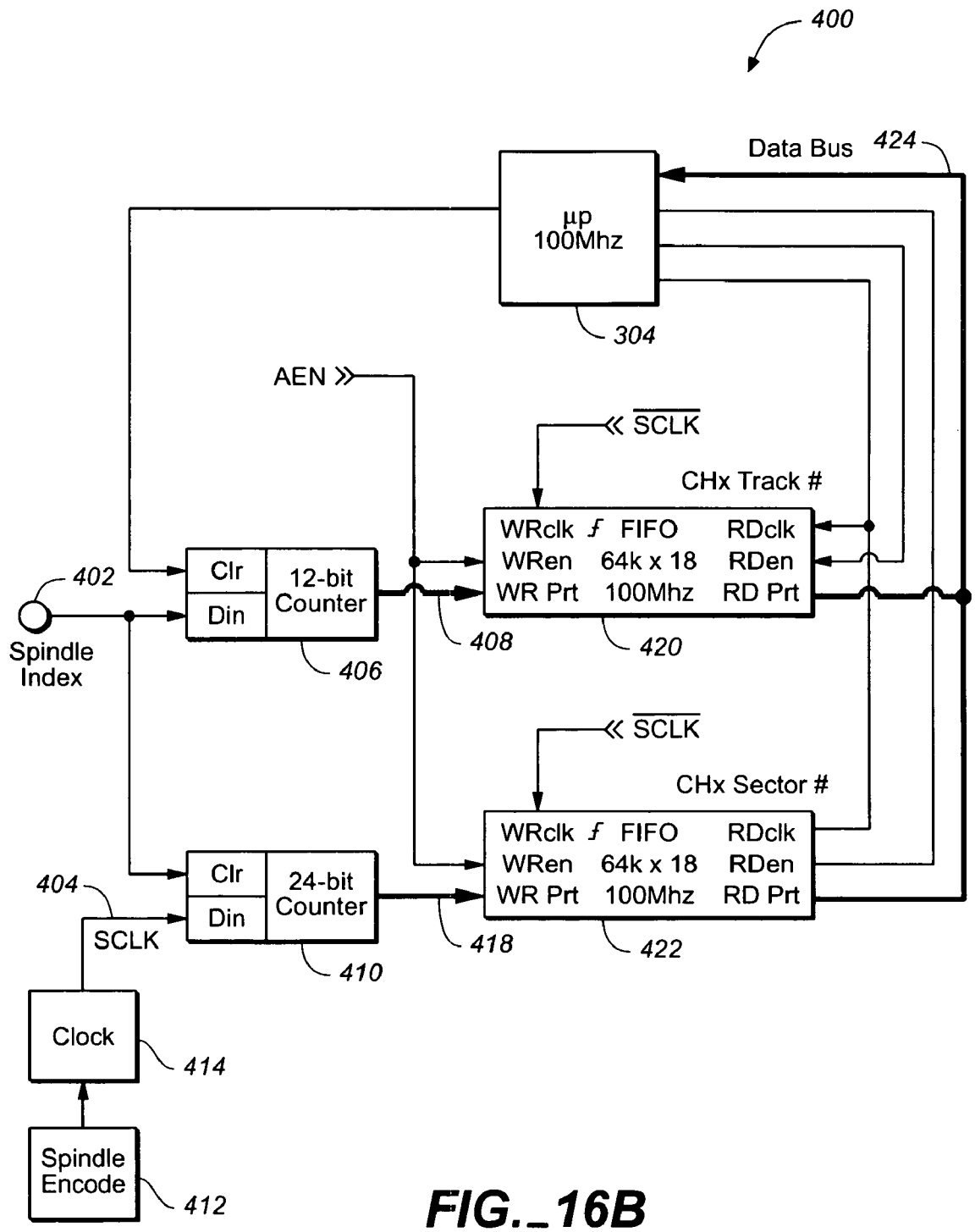
FIG._16B

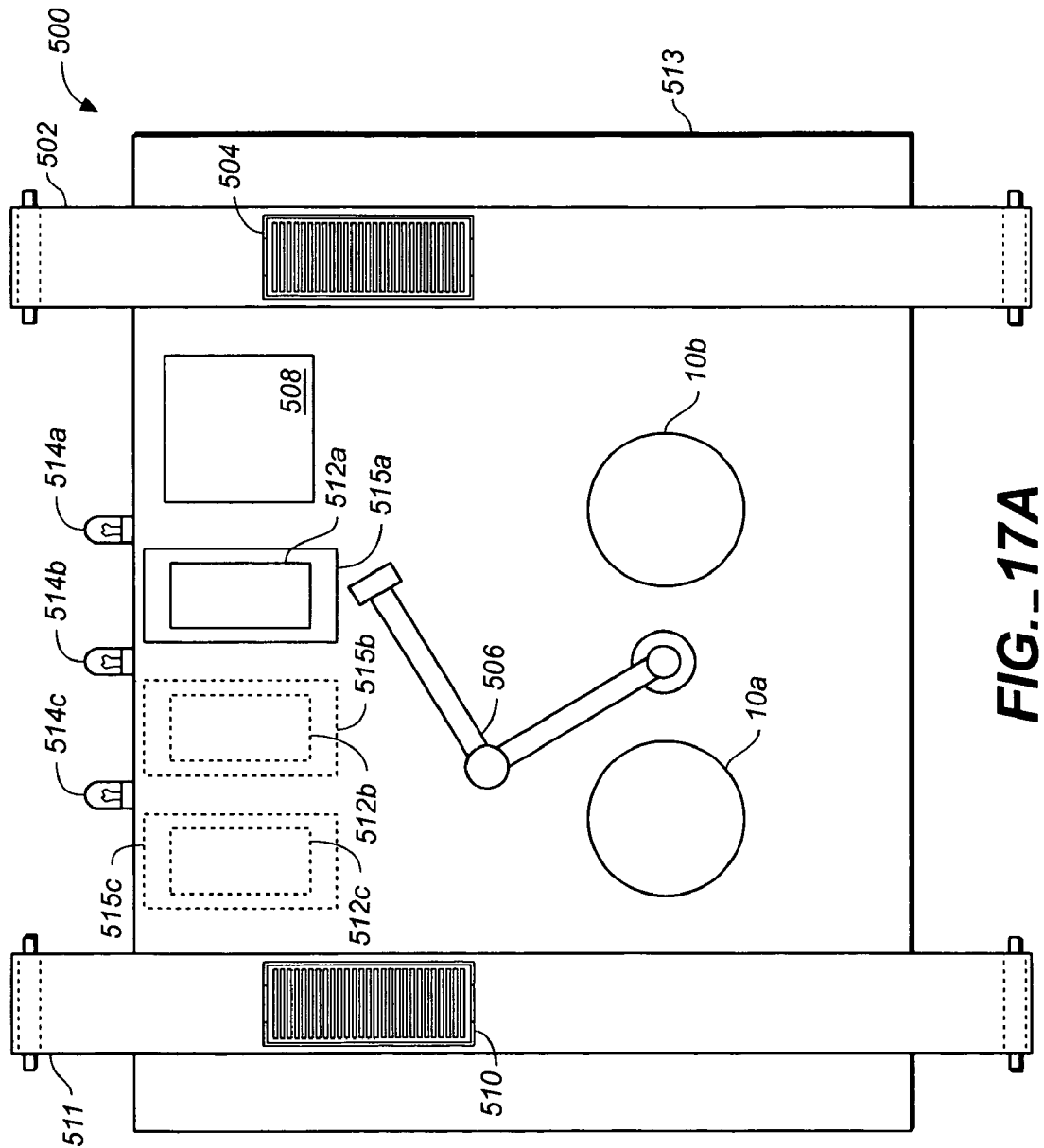
FIG._17A

TEST HEAD FOR OPTICALLY INSPECTING WORKPIECES COMPRISING A LENS FOR ELONGATING A LASER SPOT ON THE WORKPIECES

CROSS-REFERENCE TO PROVISIONAL APPLICATION

This application claims priority based on U.S. provisional patent application no. 60/643,748, filed Jan. 13, 2005.

BACKGROUND OF THE INVENTION

This invention relates to methods and apparatus for optically inspecting workpieces such as substrates used to make magnetic disks or magnetic disks during any point in the manufacturing process (including the finished disk).

Magnetic disks are typically manufactured using the following method.
1. A disk-shaped substrate (typically an Al alloy) is lapped or ground.
2. A material such as a nickel phosphorus alloy is plated onto the substrate.
3. The plated substrate is polished and textured. (During texturing, texture grooves are typically formed in the substrate by mechanical abrasion to cause a subsequently deposited magnetic layer to exhibit anisotropy. It is also known to laser texture substrates for tribological reasons)
4. One or more underlayers, one or more magnetic layers and one or more protective overcoats are deposited onto the plated substrate. (The deposition process can comprise sputtering or other techniques.) Other layers can also be deposited onto the substrate during manufacturing.
5. A lubricant is applied to the disk.

At various points during manufacturing (e.g. before or after texturing), it is desirable to inspect the substrate for bumps, pits, contaminant particles, or other defects. During such inspection, one should be able to detect very small defects. It is known in the art to use lasers to scan such substrates for this purpose. See, for example, U.S. Pat. Nos. 6,566,674 and 6,548,821, issued to Treves et al. (The Treves patents are incorporated herein by reference.)

During use, a motor rotates a disk substrate while a laser beam reflects off the substrate. A detector detects the laser light after it reflects off of the substrate. An output signal provided by the detector is used to determine whether there are defects on the substrate surface. During this process, the laser beam moves relative to the spinning disk. In this way, the beam can scan the entire disk surface.

SUMMARY

An optical inspection head comprises a laser source for providing a laser beam that passes through a cylindrical lens for altering the shape of the spot formed on a workpiece. (Typically, after passing through the cylindrical lens, the laser beam passes through a second lens that concentrates the laser beam onto the workpiece.) The laser beam typically repeatedly passes a point on the workpiece, but each pass is displaced from the previous pass in a first direction. Of importance, the cylindrical lens a) increases the laser spot size in the first direction; and b) causes the laser spot to be out of focus in the first direction (although the laser spot is typically in focus in a second direction substantially perpendicular to the first direction). The size of the laser spot in the first direction is insensitive to the position of the cylindrical lens along the optical path of the laser beam.

The workpiece is typically disk-shaped and rotates while the laser beam is applied to it. The first direction is typically substantially parallel to the radial direction of the workpiece. Motion of the laser beam relative to the workpiece in the first direction can be constant or not constant (e.g. periodically starting and stopping). Because the spot size is increased in the first direction, it takes less time to scan the entire workpiece surface than if the spot size were circular.

Apparatus in accordance with the invention is used for inspecting a surface of a workpiece using light reflected off the workpiece surface. As used herein, the term "inspect" includes testing a workpiece surface for the presence of defects; evaluating the surface; collecting data concerning the surface of the workpiece; and/or determining whether the surface is suitable, based on one or more criteria.

In one embodiment, one or more detectors detect light that is specularly reflected off the workpiece surface, and one or more detectors detect light that is scattered by defects on the workpiece surface.

In one embodiment a method and apparatus in accordance with the invention are used to inspect substrates used for magnetic disk manufacturing. However, the method and apparatus can also be used to inspect a magnetic disk at any portion during the manufacturing process, for example a) an aluminum substrate prior to being plated with NiP; b) the substrate after plating with NiP but before being polished and textured; c) the substrate after polishing but before texturing; d) the substrate after texturing but before sputtering of the underlayer, magnetic layer and protective overcoat, e) the disk after sputtering but before application of a lubricant; or f) the finished disk. There are several points during which the disk is washed. Inspection can occur before or after washing. As used herein, the term "platter" encompasses a disk at any point during or after manufacturing (including disks made using non-aluminum substrates, disks made using deposition processes other than sputtering, disks used in conjunction with vertical recording, disks used in conjunction with longitudinal recording, textured disks and untextured disks).

DESCRIPTION OF THE DRAWINGS

FIGS. 1A and 1B schematically illustrate optical inspection apparatus including an optical inspection head for inspecting a workpiece. FIG. 1A is an exploded perspective drawing.

FIGS. 2A and 2B schematically illustrate the optical paths and optical elements within the optical inspection head of FIGS. 1A and 1B. FIG. 2A shows the optical paths and elements from a perspective view. FIG. 2B shows the optical paths and elements in plan view.

FIGS. 3A to 3D are perspective views of a monolithic block of material forming the optical inspection head of FIGS. 1 and 2.

FIG. 4 illustrates a platter having a surface with two scratches thereon.

FIGS. 5A and 5B illustrate a block of material during a portion of a manufacturing process in accordance with the invention.

FIG. 5C illustrates a structure for mounting a mirror in one of the optical paths.

FIG. 6A schematically shows the optical path between a platter and an optical detector comprising two lenses for collecting and concentrating light.

FIG. 6B schematically shows the optical path between a platter and an optical detector comprising one lens that both collects and concentrates light.

FIG. 7 illustrates two optical heads inspecting upper and lower platter surfaces in accordance with an alternative embodiment of the invention.

FIG. 8 illustrates paths traced by upper and lower laser beams on a platter.

FIGS. 9 and 10 illustrate the placement of lenses in a lower test head in accordance with the invention.

FIG. 11 illustrates the point on an innermost track where a laser strikes a platter.

FIG. 12 illustrates the juxtaposition of the upper and lower heads and the platter in plan view.

FIG. 13 schematically illustrates in plan view a quad detector for detecting specularly reflected laser light within an embodiment of the optical inspection head.

FIG. 14 schematically illustrates a circuit for processing output signals from the quad detector of FIG. 13.

FIG. 15A schematically illustrates a circuit for providing selected data corresponding to the output signals of optical detectors to a processing device.

FIG. 15B schematically illustrates a circuit for providing selected location information to the processing device.

FIGS. 16A and 16B schematically shows circuitry details that can be used in the circuits of FIGS. 15A and 15B.

FIG. 16C illustrates a logic circuit that can be used in conjunction with the circuit of FIGS. 16A and 16B FIGS. 17A and 17B illustrate first and second embodiments of robotic cells used in conjunction with the test heads of the present invention.

DETAILED DESCRIPTION

Figure 17B:
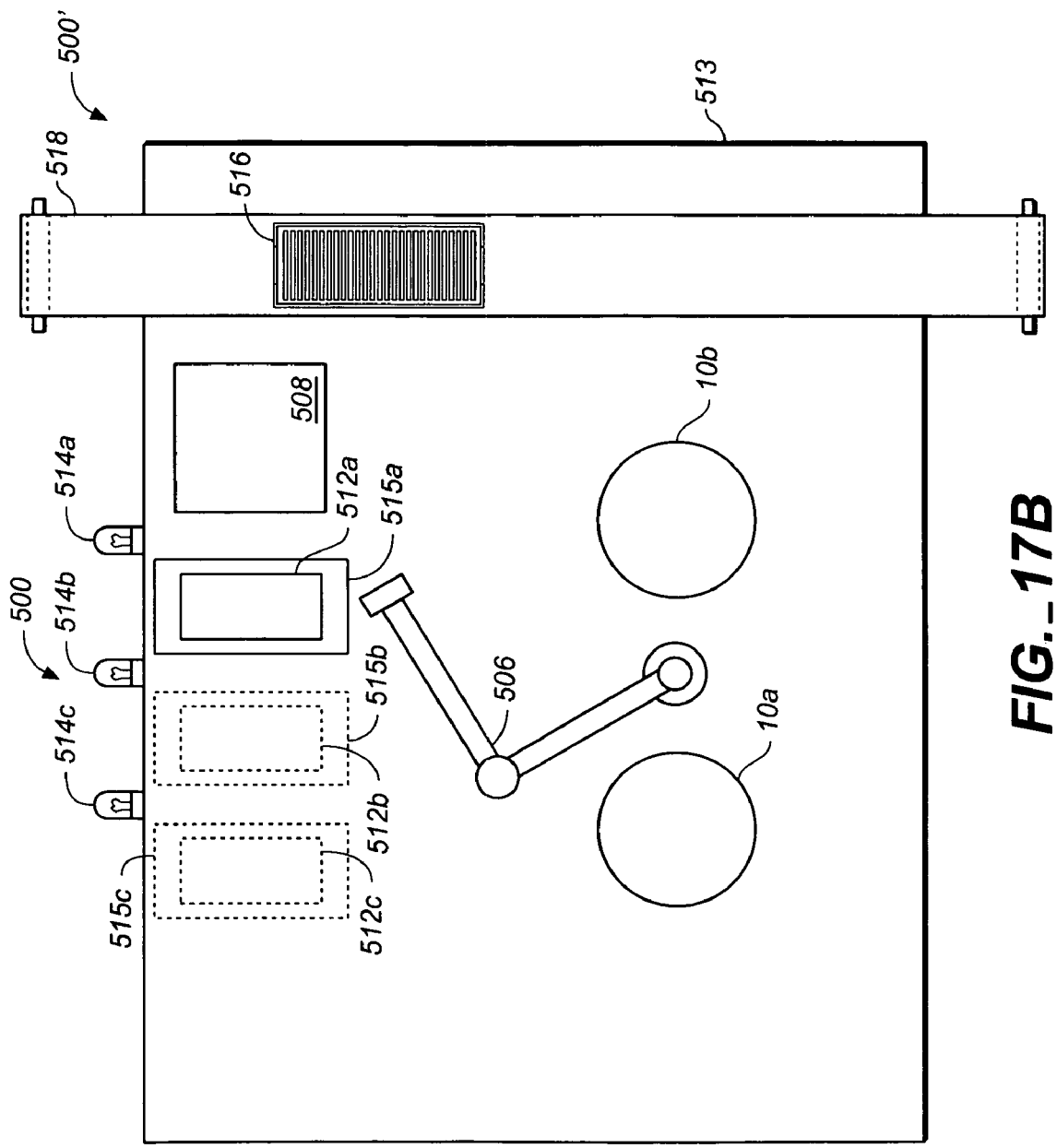

I. Overview of Optical Inspection Apparatus 10

FIGS. 1A, 1B, 2A and 2B schematically illustrate an example of an optical inspection apparatus 10 in accordance with the invention that includes a head 12 for optically inspecting a top surface 13*u* of a workpiece 13 (typically a platter). (FIGS. 1A and 1B show the exterior of head 12 in schematic form. The actual appearance of head 12, in one embodiment, is shown in FIGS. 3A to 3D. FIGS. 2A and 2B show the optical paths and elements within head 12.) Head 12 comprises a laser source 14 for providing a laser beam 16. Head 12 also includes a) a set of lenses, masks, mirrors and other optical elements (described below) for modifying laser beam 16 and directing and focusing beam 16 onto a spot on surface 13*u*; and b) a set of mirrors, lenses and other optical elements (also described below) for modifying and directing light reflected by surface 13*u* to various detectors 20-26 (discussed below). (As used herein, "reflected" includes specularly reflected light and/or scattered light.) Output signals O20-O26 from detectors 20-26 are processed to determine the condition of surface 13*u*.

Head 12 is typically constructed from a monolithic block of material, and as mentioned above, it can have an exterior appearance as shown in FIGS. 3A to 3D.

In one embodiment, laser source 14 is a solid state laser (e.g. a diode laser) having a wavelength of 660 nm. However, in other embodiments, different types of laser sources (such as a gas laser) and different types of laser light (including light outside the visible range) can be used. The laser spot on surface 13*u* can be elliptical or can have another shape. In one embodiment the laser spot is substantially elliptical, and can be 8 µm in the azimuthal direction of platter 13, and 25 to 30 µm in the radial direction of platter 13. The laser can be linearly polarized, circularly polarized or randomly polarized.

In the exemplary apparatus of FIGS. 1A to 1C, the laser light reflects off of platter 13, and is directed to a deflection detector 20, a small angle scatter detector 22, a wide-angle (approximately 90°) scatter detector 24, and a back scatter detector 26. (Referring to FIG. 1A, the small angle detector 22 typically detects scattered light within a cone whose sides form an angle α with the central ray of the reflected beam, where α is a value between 5 and 30°) Deflection detector 20 can be a bi-cell detector as described in the above-mentioned '674 or '821 patents. Alternatively, detector 20 can be a quad cell detector or other type of device, e.g. for detecting laser beam deflection along one or two directions. Detectors 22, 24 and 26 can be photodiodes, photomultipliers, avalanche photodiodes, phototransistors, etc. In one embodiment, an avalanche photodiode such as device model no. 197-70-74-5.91, manufactured by Advanced Photonix is used. The output signals from detectors 20, 22, 24 and 26 are provided to associated amplifiers A20, A22, A24 and A26, which in turn provide output signals O20, O22, O24 and 026 to circuits C20, C22, C24 and C26, respectively, for processing. Circuits C20-C26 are described below.

During use, a spindle motor M rotates a spindle S, which in turn rotates platter 13. Concurrently, laser beam 16 moves in a direction of arrow A1 relative to platter 13 to thereby sweep across platter surface 13*u*. Accordingly, the entire usable portion of surface 13*u* is scanned by laser beam 16 to thereby inspect surface 13*u* for defects. In one embodiment, platter 13 moves in a direction A2 while it rotates, and head 12 remains stationary. In another embodiment, head 12 moves in direction A1 while platter 13 merely rotates. In yet another embodiment, head 12 and platter 13 simultaneously move in directions A2 and A1, respectively, while platter 13 rotates. In yet another embodiment, the angle of laser beam 16 changes so that beam 16 sweeps across surface 13*u* while platter 13 rotates. Of importance, however, there is relative translational motion between laser beam 16 and platter 13 which permits surface 13*u* to be inspected. In yet another embodiment, the laser sweeps in directions along two axes while platter 13 is stationary. However, preferably, platter 13, motor M and spindle S are moved in direction A2 by a stepper motor, linear motor, or other type of motor (not shown) while head 12 remains stationary.

FIG. 1 only shows an upper test head 12 for testing top surface 13*u* of platter 13. However, in one embodiment, a similar lower head is provided below platter 13 for simultaneously inspecting the bottom surface of platter 13 (e.g. as shown in FIG. 7). In such an embodiment, the lower head can be slightly different from the upper head for reasons described below.

II. Detailed Description of Optical Paths of Laser Beam 16

Referring to FIGS. 2A and 2B, after laser beam 16 leaves diode laser 14, it passes through slit masks 50 and 52, reflects off a mirror 54, and passes through optional optical elements 56. Optical elements 56 comprise a glass plate 56*a*, a circular polarizer 56*b* (typically a quarter wave retarder) mounted on plate 56*a*, and a cylindrical lens 56*c* having one planar surface mounted on polarizer 56*b*. (Although elements 56 comprise structures 56*a*, 56*b* and 56*c* affixed to one another, in other embodiments they need not be affixed to one another. Structures 56*a*, 56*b* and 56*c* are separately shown schematically in FIG. 2B.)

Cylindrical lens 56*c* permits control of the shape of the laser spot on platter 13, as described below. Polarizer 56*b* circularly polarizes laser beam 16. This makes head 12 less sensitive to the direction of scratches in platter 13, e.g. as described below.

After passing through optional elements 56, beam 16 passes through a lens 58 for focusing beam 16 onto platter 13 and through a mask 60 (not shown in FIG. 2A, but shown in FIG. 2B). Beam 16 then strikes platter 13. (The angle of incidence of beam 16 is typically not perpendicular to platter 13, and in one embodiment it can be about 45° with respect to platter 13.) As described below, some of beam 16 specularly reflects off of platter 13 and some of beam 16 is scattered by platter 13 (e.g. if there are defects on the platter surface). The specularly reflected portion of laser beam 16, along with a portion of the laser light scattered off of platter 13 at a relatively narrow angle, passes through a collecting lens 62. The light passing through collecting lens 62 is hereafter referred to as light 16-1. A portion of light 16-1 strikes a small angled mirror 64 (not shown in FIG. 2A, but shown in FIG. 2B). Because mirror 64 is small, an outer portion 16-1' of light 16-1 does not strike mirror 64, but instead travels past the outer perimeter of mirror 64, reflects off a mirror 66, passes through a lens 68 and an iris 70 and then strikes detector 22. (Lens 68 concentrates light 16-1' on detector 22.) In this way, detector 22 receives light scattered off of platter 13 at relatively narrow angle α. (As mentioned above, portion 16-1' of light 16-1 is scattered. If platter 13 were perfectly smooth, portion 16-1' would have an intensity of zero.)

Inner portion 16-1" of light 16-1 reflects off of mirror 64 and strikes quad-cell detector 20 (described in greater detail below). Detector 20 detects small changes in the angle of specular reflection of portion 16-1", which in turn indicate whether relatively large bumps or pits are present on platter 13. (Portion 16-1" is light that specularly reflects off of platter 13.) Quad-cell detector 20 also detects any changes in the amount of power of portion 16-1". Such a change of power could result from fluctuation in the power provided by laser diode 14 or the presence of an area of platter 13 that exhibits reduced reflectivity (e.g. a stain).

Although the above-described embodiment uses a small mirror 64, in another embodiment, mirror 64 is much larger, but contains a small opening for transmitting specularly reflected light portion 16-1". The transmitted light in this embodiment (portion 16-1") passes to quad-cell detector 20, while the mirror reflects light portion 16-1' to detector 22.

Concurrently, a portion 16-2 of the laser light scatters off platter 13, is collected by a lens 72, reflects off a mirror 74, and passes through a lens 76 which concentrates portion 16-2 onto detector 24. Concurrently, a portion 16-3 of the laser light back scatters off platter 13, is collected by a lens 77, reflects off a mirror 78 and is concentrated by a lens 80 onto detector 26.

As mentioned above, portions 16-1' and 16-2 are light scattered at small and wide angles respectively by defects in platter 13. Portion 16-3 is light that is back scattered by defects in platter 13. Portion 16-1" is light that specularly reflects off of platter 13. Portion 16-1" indicates the angle of the walls of relatively large defects in platter 13. The magnitudes of portions 16-1', 16-1", 16-2 and 16-3 are used to determine various characteristics of different kinds of defects in the surface of platter 13.

Elements 50-80 are part of head 12, and are rigidly held within an enclosure 82. In one embodiment, enclosure 82 is a monolithic block of material such as aluminum. (Although FIGS. 1 and 2A schematically show the monolithic block as having the approximate shape of a rectangular prism, the exterior is typically as shown in FIG. 3.) Head 12 is mounted on apparatus 10 such that head 12 can be adjusted (manipulated) with three degrees of freedom as follows: a) translational motion along the Z axis for focusing, b) tilt about the X axis; and c) tilt about the Y axis. Thus, head 12 can be easily manipulated without having to individually adjust the position and angle of the optical components within the head. Only a small number of adjustments is used to couple head 12 to apparatus 10.

Although head 12 is adjustable with only three degrees of freedom, in another embodiment other adjustments are possible. In yet another alternative embodiment, head 12 can be adjusted only along the Z axis. In yet another alternative embodiment, the position of detector 20 and/or laser source 14 are adjustable, e.g. by using screws extending into head 12 (not shown) to make fine adjustments.

III. Cylindrical Lens 56c

As mentioned above, in one embodiment, cylindrical lens 56c is provided in the input optical path of laser beam 16. Lens 56c facilitates control of the shape of the light spot on platter 13. Typically, a laser beam provided by a laser diode can have an aspect ratio of about 3:1. As explained below, laser beam 16 typically strikes platter 13 at an angle (e.g. at about 45°) so that if laser beam 16 were not otherwise modified, the laser spot on platter 13 would have an aspect ratio of about 2.1:1. Lens 56c increases the aspect ratio of beam 16. In one embodiment, the aspect ratio of the laser spot on platter 13 is greater than 2.5:1, e.g. between about 4:1 and 5:1. The major axis of the laser spot is substantially parallel with direction of relative translational motion between platter 13 and laser beam 16, i.e. direction A1. Because of this, it requires less time for laser beam 16 to scan surface 13u than if the aspect ratio were less than 4:1. (The aspect ratio is preferably kept at or below 5:1 because if the aspect ratio were too large, the energy density of the laser beam would be insufficient to adequately inspect surface 13u.)

In one embodiment, cylindrical lens 56c functions in two ways. First, lens 56c reduces the beam length in the radial direction as it hits focusing lens 58, and thereby causes the beam length in the radial direction to increase as it hits platter 13. Second, lens 56c causes the laser spot on platter 13 to be out of focus in the radial direction. (The laser spot is typically in focus in the circumferential direction.) Of importance, the combination of these two effects causes the spot size in the radial direction to be substantially insensitive to the position of cylindrical lens 56c along the input optical path. For example, during experiments, one could move lens 56c by 60 mm along the input optical path without altering the major axis length of the beam spot by more than a micron.

IV. Polarization of Laser Beam 16

As mentioned above, optionally, laser beam 16 is circularly polarized, e.g. by passing beam 16 through plate 56b. If beam 16 is linearly polarized, the output signal from the various detectors will vary depending upon whether a scratch in surface 13u is parallel or perpendicular to the electric field component of the laser light. For example, referring to FIG. 4, a scratch S1 extending along a circumferential direction of surface 13u will have a different effect on head 12 than a scratch S2 extending along the radial direction of surface 13u. For example, if a) laser beam 16 is linearly polarized; b) the plane of incidence is in the azimuthal direction, and c) the polarization direction is in the radial direction, more light will scatter from scratch S1 than S2 (assuming the scratches are the same). If the polarization direction is in the incidence plane, more light will scatter from scratch S2 than scratch S1. (As is known in the art, the plane of incidence is the plane defined by the incident and specularly reflected beams.) By circularly polarizing beam 16, this difference in sensitivity to scratch direction is eliminated.

V. Enclosure 82 and its Method of Manufacture

As described above, head 12 comprises mirrors, lenses and other optical elements. We have discovered a method for making head 12 in which we avoid having to individually align various optical elements within head 12. We have also discovered a method for providing head 12 in a very compact volume. For example, we have been able to construct head 12 such that width W (FIG. 1A) is extremely small, e.g. about 5.9". Length L and thickness T are 6.2" and 3.23", respectively. (These dimensions are merely exemplary.) This is advantageous because small variations in angles of various devices caused during manufacturing of head 12 have less impact on the offset of optical beam paths if the size of head 12 is minimized. Also, ensuring that head 12 is small permits minimizing the "footprint" of apparatus 10.

To illustrate a method in accordance with our invention, reference is made to FIG. 5A, which schematically illustrates a block of material 100 (again, typically a metal such as aluminum). Intersecting portions 102 and 103 of block 100 are milled out to form an input path for light to pass from diode laser 14, to mirror 54 and to platter 13. Of importance, ledges 102a and 102b are left in path 102 to provide a surface for holding masks 50 and 52. Masks 50 and 52 are dropped through an opening 102' of portion 102 and glued in place.

As shown in FIG. 5B, a corner 104 of block 100 is also milled away so that mirror 54 can be mounted at the appropriate angle on block 100, e.g. using an adhesive or other technique.

Portions 105, 106, 108 and 110 (FIGS. 3C, 3D) are also milled out of block 100 to form output paths for light heading toward detectors 20-26. Ledges are left in block 100 for holding lenses 68, 76 and 80. Optionally, ledges are also left in paths 106-110 to hold irises for embodiments in which such irises are used. These elements are inserted through openings in the milled out portions 106, 108, 110 as appropriate and glued onto their associated ledges.

Portions 111, 112 and 113 (FIGS. 3A and 3B) are also milled out of block 100 to form paths for portions 16-1, 16-2 and 16-3 of the reflected laser light. Ledges are left in block 100 for holding collecting lenses 62, 72 and 77. Lenses 62, 72 and 77 are inserted through the openings of paths 111, 112 and 113 and glued to their associated ledges as appropriate. In addition, a ledge 111a is left in path 111 for holding a glass window 64w, upon which is affixed a pedestal 64p, upon which mirror 64 is mounted (FIG. 5C). (FIG. 5C merely shows one way of holding mirror 64 within head 12. It will be appreciated that other techniques could also be used to hold mirror 64.)

Finally, side or corner portions are cut off of block 100 so that mirrors 66, 74 and 78 can be mounted at the appropriate angle on block 100, e.g. using an adhesive or other technique.

It will be appreciated that in different embodiments, the various portions of block 100 can be removed in an order other than as described above.

VI. Reduction or Elimination of Stray Light Within Head 12

In accordance with one embodiment of our invention, several techniques are used to minimize the amount of stray light that might otherwise generate noise in output signals O20-O26. (Stray light can arise from several sources. For example, diode lasers often emit a "halo" around the main laser beam 16. Also, stray light can result from unwanted reflection off of lenses, masks or other elements within head 12.) In one embodiment, black tubing is inserted into the various openings and applied to the walls of the optical paths to absorb stray light therein. The surface of the tubing is blackened by an electroplating technique. (In one embodiment, nickel is electroplated onto the tubing walls. One type of light absorptive layer is available from Epner Technology, Inc. of Brooklyn, N.Y. See also the pages from www.epner-.com submitted as Exhibit A of our provisional patent application No. 60/643,748, filed Jan. 13, 2005, incorporated herein by reference.) The black tubing constitutes a "light trap" for absorbing stray light.

In an alternative embodiment, in lieu of inserting black tubing into head 12, the interior of head 12 can be anodized to provide a dull black matte surface for the optical paths.

In one embodiment, a narrow band V-type AR (antireflective) coating is applied to the various lenses within head 12 to prevent multiple reflections. (As used herein, the term "V-type AR coating" also includes a "Super V-Type AR coating".) Such a coating is typically tailored to the wavelength of laser beam 16. Reflectivity exhibited by a lens coated in accordance with this embodiment is typically less than 0.25%.

One or more masks with slits are inserted within the optical paths or affixed to the lenses to reduce or prevent stray light which would otherwise interfere with operation of head 12.

Finally, masks or irises are provided in front of one or more of detectors 20-26. (The irises are masks that can have an opening of an adjustable size.)

The above-mentioned masks, coatings and irises prevent or reduce stray light, e.g. light that would be present in the scattered light optical paths even in the absence of a defect on platter 13. These masks, coatings and irises are designed and placed to avoid impacting or substantially impacting light caused by defects on platter 13.

In addition, one or more other masks can be provided to block light caused by a desired texture or a pattern deliberately provided on the surface of platter 13 (e.g. for discrete track recording). These masks in the output optical paths that eliminate or reduce the above-mentioned light caused by diffraction due to patterns on platter 13 can, however, block some portion of the light caused by defects.

While antireflective coatings are provided on all lenses in one embodiment, in another embodiment, antireflective coatings are only provided on some lenses, e.g. lenses 58 and 62. Similarly, in some embodiments, light trap tubing is only placed along some of the optical paths, e.g. input paths 102 and 103 and small angle scatter output paths 111 and 106. Also, in some embodiments, an iris is only provided in front of detector 22.

The importance of reducing stray light can be appreciated in light of the following. In one embodiment, an avalanche photodiode with a gain of 300 is connected to a low noise transimpedance amplifier with a feedback resistor of 10,000 ohms, followed by a post amplifier with a gain of three. The bandwidth of the system is 10 MHz. The measured electronic noise was 0.45 mV RMS, while the calculated value was 0.3 mV RMS. The measured shot noise with 118 nW of laser light impinging on the avalanche photodiode was 7.4 mV RMS, while the calculated value was 6.2 mV RMS. The shot noise is proportional to the square root of the light power. Therefore, in order to reduce the shot noise to the level of the electronic noise, the stray light should be of the order of 1 nW or less. Since the typical laser power is 20 mW, one should attempt to reduce the laser stray light to 0.0005% of the laser power.

Although some embodiments include the masks, irises, tubing for absorbing or trapping light, and/or antireflective coatings, other embodiments lack these features.

VII. Embodiment with Reduced Number of Lenses

FIG. 6A schematically illustrates platter 13, scattered light 16-2, collecting lens 72, concentrating lens 76 and detector 22. (Mirror 74 has been eliminated from FIG. 6A for ease of illustration.) If the light between lenses 72 and 76 is substantially collimated, optical distance D1 can be arbitrarily long without affecting operation of head 12. While one embodiment employs both lenses 72 and 76, in another embodiment, a single lens 72' both collects light 16-2 and concentrates light 16-2 onto detector 22 (FIG. 6B). In like manner, instead of passing light 16-3 through both lenses 77 and 80, a single lens can be used. Similarly, instead of passing light 16-1' through both lenses 62 and 68, a single lens can be used.

In the embodiment of FIG. 6B, distance D1' depends upon the focal characteristics of lens 72'. Distance D1' cannot be arbitrarily selected. Also, if lens 72' were identical to lens 72, the distance D2 between platter 13 and lens 72' would have to be greater than the corresponding distance D3 between lens 72 and platter 13. This would necessitate a loss of effective numerical aperture for lens 72' compared to lens 72.

VIII. Embodiments Comprising Two Test Heads

A. Displacement of Laser Spot on Platter

As mentioned above, in one embodiment, a single test head 12 is provided for testing upper surface 13u of platter 13. In other embodiments, a second test head 12d (FIG. 7) is provided for testing the lower surface of platter 13 while test head 12 tests the upper surface of platter 13. In one such an embodiment, head 12d is modified slightly to provide space for spindle S. Further, the position of lens 62d in head 12d is slightly offset compared to the position of lens 62 in head 12. (As used herein, the letter "d" is added to the element reference number to distinguish between a structure in lower head 12d and a corresponding structure in upper head 12.) Further, whereas in one embodiment upper laser beam 16 traces a path 122 (FIG. 8) along upper surface 13u of platter 13 (i.e. in the radial direction of platter 13), lower laser beam 16d traces a slightly different path 122d along lower surface 13d of platter 13 that is displaced by a distance D4 from such a radial path. This is done to enable the use of lens 62d with a high numerical aperture (high collection efficiency) in the presence of spindle S. (In one embodiment, distance D4 is 4.763 mm, the diameter and back focal length of lens 62d are 25 mm and 20.2 mm, respectively, and the minimum radius to be scanned is 15.5 mm. The effective diameter of lens 62d is 22 mm. Lens 62 is identical to lens 62d. These values are merely exemplary.)

FIGS. 9 and 10 illustrate a portion of head 12d in plan view (looking up) and side view, respectively. (In FIGS. 9 and 10, the optical elements associated with portions 16-2d and 16-3d of the reflected laser light as well as the elements pertaining to upper surface 13u have been eliminated for sake of clarity.) In FIGS. 9 and 10, laser beam 16d strikes a point 124d on surface 13d near the inner diameter of platter 13. (Point 124d is eclipsed, and therefore not visible, in FIG. 10.) Lens 62d receives a cone of light from point 124d at an angle β. It will be appreciated that if point 124d were not displaced from radius R of platter 13 by distance D4, angle β would be reduced because lens 62d would be further away from point 124d. Lens 62d could not be moved closer to point 124d because spindle S would be in the way. By displacing point 124d in the manner shown, one need not reduce angle η, and therefore the numerical aperture of lens 62d can be increased. This has the benefit of providing more light energy to detector 22d.

The effect described above with respect to FIGS. 9 and 10 is equivalently achieved in the manner shown in FIG. 11. Referring to FIG. 11, track 130 represents the innermost track of platter 13 that is to be scanned. (The term "track" is used herein includes embodiments in which the tracks are part of a continuous spiral and embodiments in which the tracks are discrete.) Laser beam 16d strikes point 124d on platter 13 such that the plane of incidence is not tangential with track 130. Rather, in the illustrated embodiment, the plane of incidence forms an angle θ (in one embodiment, 17.90°) with respect to track 130. By arranging the plane of incidence and track 130 as described above, one can arrange lens 62d so that track 130 can be scanned without sacrificing numerical aperture.

It is noted that the cone of light of incident laser beam 16d is much narrower than the cone of reflected light 16-1d. This characteristic of the incident and reflected beams enables being able to employ a high NA for lens 62d using the displacement technique discussed above.

As mentioned above, in one embodiment laser beams 16, 16d scan top and bottom surfaces 13u, 13d of platter 13 simultaneously. It is more important that lower laser beam 16d is displaced in the manner discussed above (or having the plane of incidence intersect with track 130 as discussed above) because spindle S (which extends below, but generally not above, platter 13) interferes with placement of lens 62d. Thus, displacement of the upper laser beam 16 is unnecessary. Although unnecessary, in some embodiments upper laser beam 16 is displaced so that heads 12 and 12d can be substantially identical. In fact, FIGS. 3A to 3D show a half-cylindrical section 132 cut out of head 12. This is useful if heads 12 and 12d are to be identical, and it allows room so that head 12d can accommodate spindle S when scanning the inner tracks of surface 13d.

Because beam 16d is displaced, the software processing the output signals from detectors 20d to 26d takes into account this displacement when generating a "map" of the characteristics of surface 13d as described below.

B. Angle of Laser Beam 16 With Respect to Beam 16d

In one embodiment, heads 12 and 12d are arranged to avoid or minimize interference of laser beam 16 on head 12d, and to avoid or minimize interference of laser beam 16d on head 12. This can be accomplished by selection of the angle of incidence of laser beams 16 and 16d on platter 13. FIG. 12 shows in plan view the juxtaposition of heads 12, 12d and platter 13. FIG. 12 also indicates a) direction A2 of travel of platter 13, b) the direction A3 of incident laser beam 16 (after leaving mirror 54) and specularly reflected laser beam 16" (prior to striking mirror 64) in the plane of platter 13, and c) the direction A4 of incident laser beam 16d (after leaving mirror 54d) and specularly reflected laser beam 16d" (prior to striking mirror 64d) in the plane of platter 13.

As can be seen directions A3 and A4 are at an angle γ such that beams 16" and 16d" travel in different directions. (Angle γ is typically greater than 0° but less than 20°.) This angle reduces the probability that light scattered from one side of platter 13 will travel to the collection lenses on the other side of platter 13 when beam 16 is near the outer edge of the platter. Advantageously, this prevents "cross communication" or interference between laser light in head 12 from affecting head 12d and vice versa.

As can be seen in FIG. 12, directions A3 and A4 are somewhat close to being antiparallel. Thus, in the embodiment of FIG. 12, heads 12 and 12d can be identical, with head 12d being a "flipped over" version of head 12. The facts that a) directions A3 and A4 are close to antiparallel; b) beam 16 travels generally away from mirror 64d; and c) beam 16d travels generally away from mirror 64 also serve to prevent cross-interference between heads 12 and 12d (especially when beams 16 and 16d strike points close to the outer diameter of platter 13). However, in another embodiment, however, directions A3 and A4 need not be close to antiparallel.

FIG. 12 shows that points 124, 124d are displaced from one another by distance D4 (discussed above). However, in an alternate embodiment, spot 124 is directly over spot 124d. In yet another embodiment, spots 124 and 124d are displaced by a distance of two times D4. (In such an embodiment, heads 12 and 12d can be identical.)

Although directions A3 and A4 form angle γ, in one embodiment, directions A3 and A4 are antiparallel. In yet another embodiment, directions A3 and A4 are closer to parallel than antiparallel, but still form an angle γ with respect to one another.

IX. Quad Detector 20 and Circuit C20

In one embodiment, detector 20 is a quad detector 20 such as a semiconductor device having four regions 20-1, 20-2, 20-3 and 20-4 (FIG. 13). A spot 150 of portion 16-1" of laser light 16 strikes detector 20 as described above. If laser beam 16 strikes a defect on surface 13u, depending upon the slope of the defect walls, spot 150 will be deflected away from the center C of detector 20. If spot 150 is deflected in a direction A5, the output signal from region 20-2 will be greater than the output signals from regions 20-1, 20-3 and 20-4. If a steeper defect is encountered by beam 16 on surface 13u, spot 150 will move further in direction A5, and the output signal from region 20-2 will be greater than it would have been if a less steep defect was encountered.

If a defect causes spot 150 to be deflected in direction A6, the output signal from region 20-1 will exceed that of regions 20-2 to 20-4. In this way, detector 20 provides signals to circuit C20 indicating the direction and steepness of a wall of a defect on surface 13u.

In one embodiment, circuit C20 includes analog circuits 200, 201 and 202 (FIG. 14) which generate signals S200, S201 and S202 proportional to (I1+I2), (I3+I4) and (I1+I2)−(I3+I4), respectively, where I1, I2, I3 and I4 are the amounts of light striking regions 20-1, 20-2, 20-3 and 20-4, respectively. Signal S202 indicates the extent to which portion 16-1" of laser light is deflected upward or downward, e.g. by defects in the surface of platter 13. Circuit C20 also includes analog circuits 203, 204 and 205, which generate signals S203, S204 and S205, proportional to (I1+I3), (I2+I4) and (I1+I3)−(I2+I4), respectively. Signal S205 indicates the extent to which portion 16-1" of the laser light is deflected to the left or right. Circuit C20 also includes analog circuit 207 which generates an electrical signal S207 having a voltage proportional to (I1+I2+I3+I4). Signal S207 represents the total amount of light striking detector 20. Signals S202 and S205 are typically normalized (e.g. divided by) the value I1+I2+I3+I4 (S207) so that the apparatus is insensitive to laser output power fluctuations and reflectivity variations of regions of platter 13. Normalization can be done using analog techniques. However, signals S202, S205 and S207 can also be digitized (e.g. using an analog to digital converter), and normalization can be done digitally, e.g. using a computer as described below.

As mentioned above, in one embodiment, circuits 200-207 sum and subtract various signals using analog techniques. However, in other embodiments, signals I1 to I4 can be digitized, and the summing and subtraction can also be done digitally. As discussed above, the summing and subtraction are typically done in a plurality of stages (e.g. summing first, subtracting second). However, in other embodiments, these functions can be performed in one stage.

X. Description of Circuits C22, C24 and C26

Circuits C22, C24 and C26 (for processing the output signals of detectors 22-24) are identical. FIG. 15A illustrates circuit C22. As can be seen, output signal O22 from detector 22 is provided to an analog-to-digital converter 300, which provides its output data to a FIFO memory 302. The output of FIFO memory 302 can be asynchronously read by a microprocessor 304. In this way, microprocessor 304 reads data from FIFO memory 302 corresponding to the output signal provided by detector 22. Microprocessor 304 provides these data to a general purpose processor 306 via a high speed bus interface circuit 308 and a bus 310 (in one embodiment a USB bus). (Processor 306 then performs additional processing on the data from FIFO memory 302.) In one embodiment, microprocessor 304 is a device such as model C8051F120, available from Silicon Laboratories, and has a clock speed of 100 MHz. However, other microprocessors can also be used. Also, while processor 306 is typically a general purpose processor, alternatively, it can be a digital signal processor, e.g. a Texas Instruments TMS320F2812, which can operate at 150 MIPS.

Interface circuit 308 receives data on a set of buses 312, which are driven by microprocessors in circuits C20, C24 and C26 similar to microprocessor 304.

Advantageously, in one embodiment, digital values of signal O22 are only stored in FIFO memory 302 when signal O22 exceeds a threshold signal THR. This is an advantage because it enables efficient use of FIFO memory 302 by storing only data that are of interest for evaluating characteristics of platter 13. Thus, by only selecting these digital values, the memory and processor requirements of circuit C22 and processor 306 are reduced. The manner in which this is accomplished is as follows. As seen in FIG. 15A, a write data enable signal DEN for FIFO memory 302 is provided by an analog comparator 316. Signal DEN is only active when signal O22 from detector 22 exceeds threshold signal THR. Thus, data are only stored in FIFO memory 302 when signal O22 exceeds signal THR.

Signal THR is an analog signal generated by digital to analog converter 318, which in turn is controlled by microprocessor 304. Thus, microprocessor 304 controls the magnitude of signal THR. Signal THR is user-selectable so that only events of interest are passed. (In general, signal THR is made to be greater than the signal noise level.) Optionally, in one embodiment, microprocessor 304 or processor 306 establishes the value of signal THR in response to the measured noise present in signal O22.

It is typically desirable to provide location data to processor 306 indicating the location on platter 13 that causes signals O22-O26 to exceed their associated threshold values THR. In one embodiment, this is done by providing a "track address" (identifying the position on surface 13u in a radial direction) and a "sector address" (identifying the position on surface 13u in a circumferential direction) to processor 306 where the conditions of surface 13u cause signal O22 to exceed threshold signal THR. In one embodiment, circuitry is provided which indicates the start location (track and sector address) of an area on surface 13u where signal O22 begins to exceed signal THR, and the end location on surface 13u where signal O22 falls below signal THR.

FIG. 15B illustrates address circuit 400 for providing the start and stop addresses. Circuit 400 includes a spindle index input lead 402 and a sample clock input lead 404. Spindle index input lead receives a pulse every time platter 13 completes a revolution. These pulses are counted by a counter 406, which provides a track address on a track address bus 408 in response thereto. The track address is the number of the track currently scanned by laser beam 16.

A second counter 410 receives input pulses from sample clock input lead 404. In one embodiment, these pulses are provided at a rate of 249,856 pulses per platter revolution, although this number is merely exemplary. The sample clock pulses are synchronized with the disk rotation. In one embodiment, this is accomplished by providing an optical spindle encoder schematically represented as box 412 coupled to spindle S. This encoder provides 512 pulses per platter revolution. A clock circuit 414 is coupled to receive these pulses and generate the sample clock pulses in response thereto using a phase-locked loop to create an in-phase multiple of the spindle encoder pulses. Counter 410 counts the sample clock pulses and provides a sector address on a bus 418.

The track and sector addresses are stored in FIFO memories 420 and 422, respectively in response to signal AEN. (Signal AEN goes active when signal O22 first exceeds threshold THR, and again when signal O22 falls below threshold THR. Thus, signal AEN represents the beginning and end locations of a defect on surface 13u.) Microprocessor 304 asynchronously reads the track and sector addresses from FIFO memories 420 and 422 via a bus 424. These addresses are then provided by microprocessor 304 to processor 306 via interface circuit 308 and bus 310.

As mentioned above, separate counters 406, 410 are used to generate track and sector addresses. However, in an alternate embodiment, a single counter can be used to generate both the track and sector addresses. (In one such an embodiment, the sector address is Q modulus N, where Q is the value stored in the single counter and N is the number of sectors per revolution. The track address is the integer portion of Q/N.) The output from this single counter can be provided to a FIFO memory of appropriate width. (Alternatively, one can construct a counter in which the lower counter bits constitute the sector address, the upper counter bits constitute the track address and only increment when the lower bits reach the value N, and the lower bits reset upon reaching N.)

As mentioned above, signal O22 in analog form is compared to threshold signal THR. However, in an alternative embodiment, signal O22 is digitized (or otherwise provided in digital form) and threshold THR is in the form of a digital value. The digitized signal O22 is compared with this digital threshold THR value to generate signals AEN and DEN.

Although in some embodiments, signal THR can be changed by microprocessor 304, in other embodiments, signal THR cannot be changed.

While the above-described embodiments pass information to the various FIFO memories whenever signal O22 exceeds signal THR, in some embodiments, information is only passed to the FIFO memories when signal O22 is less than an upper threshold value. In yet another embodiment, information is only passed to the FIFO memories when signal O22 is simultaneously greater than signal THR and less than an upper threshold value. In yet another embodiment, information is only passed to the FIFO memories when signal O22 is either less than signal THR (a lower threshold) or greater than an upper threshold value.

As mentioned above, circuit C20 (which processes output signals from quad detector 20) provides output signals S202 and S205 (corresponding to the vertical and horizontal deflection of portion 16-1" of laser beam 16) and signal S207 (corresponding to the total amount of power within portion 16-1"). Signals S202 and S205 are provided via an amplifier to circuits that are substantially identical to two iterations of circuit C22 (one for signal S202, and one for signal S205), where they are digitized and passed to microprocessor 304 and processor 306 if they exceed associated threshold voltages.

Signal S207 is passed to microprocessor 304 of circuit C20 and processor 306 whenever signal S202 or S205 is converted to a digital value, stored in a FIFO memory which is asynchronously read by microprocessor 304 and passed on to processor 306. In this way, signals S202 and S205 can be normalized by processor 306.

XI. Detailed Description of an Embodiment of Circuits C22-C24

FIGS. 16A and 16B illustrate in greater detail the structure of FIGS. 15A and 15B. In FIGS. 16A and 16B, WRclk, Wren, WR Prt, RDclk, Rden and RD Prt refer to the write clock, write enable, write port, read clock, read enable and read port. The counter input CIR resets counters 406 and 410. The input Din increments counters 406 and 410. Signal SCLK is generated from clock circuit 414. FIG. 16C shows a write enable sequence logic circuit 426 that can be used to generate signals DEN and AEN. Circuit 426 is useful because analog to digital converter 300 typically exhibits a finite pipeline delay of several cycles of clock signal SCLK. Circuit 426 facilitates proper loading of the FIFO memories given this pipeline delay. As shown in FIG. 16C, in one embodiment circuit 426 comprises a network of serially connected D-type flip-flops 427 that generate signals DEN and AEN in such a manner that these signals only go active if signal O22 exceeds threshold signal THR for a certain amount of time. (As mentioned above, signal DEN enables writing data to FIFO memory 302. Signal AEN enables writing data to FIFO memories 406 and 410.) Each of D Flip-flops 427 stores the out put signal of comparator 316 delayed by an associated number of pulses of clock signal SCLK. Circuit 426 provides two gating signals, one for generating signal DEN and one for generating signal AEN. The timing for signals DEN and AEN are generated from the output signal of comparator 316 and the pulse train that constitutes signal SCLK. In particular, signals DEN and AEN are based on selected states of the flip-flops 427. (For example, signal DEN is the output of comparator 316 delayed by four pulses of clock signal SCLK. Signal AEN comprises one pulse on the rising edge of signal DEN and one pulse immediately before signal DEN falls.) The circuit shown in FIG. 16C is merely exemplary.

XII. Robotics Used in Conjunction with Head 12

FIG. 17A schematically illustrates a "cell" 500 for testing platters in a manufacturing environment. A conveyor 502 provides cassettes 504 of platters 13 to be inspected. A robotic arm 506 provides platters 13 to either test apparatus 10a or test apparatus 10b. (Both apparatus 10a and 10b typically comprise both upper and lower heads 12, 12d for testing both sides of platters 13.) After test apparatus 10a tests a platter 13, arm 506 grabs platter 13 and places it either in a reject container 508, a pass cassette 510, or a further evaluation cassette 512a. (Typically, the vast majority of platters, e.g. more than 90% of the platters, should be placed in pass cassette 510.) The platters deposited in reject container 508 are not necessarily handled with the degree of care that would be needed if the platters were to be subjected to further manufacturing steps. However, the platters in cassettes 510 or 512*a* are typically maintained with such care. After arm 506 moves a platter 13 from apparatus 10*a* to one of cassettes 510 or 512*a* or container 508, arm 506 takes another platter 13 from cassette 504 and places it in test apparatus 10*a* to be evaluated.

In like manner, after test apparatus 10*b* evaluates a platter 13, arm 506 places that platter either in reject container 508, or one of cassettes 510 or 512*a*, depending upon the outcome of testing. Thereafter, arm 506 takes another platter from cassette 504 and places it in apparatus 10*b*.

Advantageously, container 508 has a very large capacity and does not need to be replaced often. Thus, it is unnecessary to shut down cell 500 very often to empty container 508.

Although FIG. 17A shows robotic arm 506 servicing two test apparatuses 10*a*, 10*b*, in alternative embodiments, cell 500 may comprise one or more test apparatuses, with arm 506 servicing the additional apparatuses. Also, although FIG. 17A shows cassette 512*a* for further evaluation, in other embodiments, several cassettes can be provided for receiving platters that are to be subjected to further evaluation (e.g. optional cassettes 512*b* and 512*c*, shown in phantom). Platters 13 may be placed in different ones of these cassettes depending upon specific characteristics of their surfaces as determined by test apparatus 10*a*, 10*b*. Also, although FIG. 17A shows one reject container 508, in other embodiments, a plurality of reject containers 508 can be provided. Also, although FIG. 17A shows only one arm 506, a plurality of arms can be provided in cell 500 for moving platters. For example, one of the arms can provide platters to test apparatus 10*a*, 10*b*, and another arm can provide platters to container 508 and/or cassettes 510 and 512*a*.

A safety enclosure 513 surrounds cell 500 to prevent injury to manufacturing personnel. In one embodiment, conveyor mechanisms 502 and 511 continuously carry new cassettes 504 and 510 into the area protected by enclosure 513.

An alarm 514*a* indicates if cassette 512*a* is full. Alarm 514*a* can provide an audible signal. Alternatively, alarm 514*a* can be a light that illuminates to indicate that cassette 512*a* is full. (Alarm 514*a* can be actuated either by a sensor that determines that cassette 512*a* is full, or by a counter that determines that cassette 512*a* is full by counting the platters therein. Alarm 514*a* can be an LED, a small incandescent bulb, or other optical display element.) However, during the time between the actuation of alarm 514*a* and replacement of cassette 512*a*, robotic arm 506 places platters that would otherwise be placed in cassette 512*a* into container 508. In this way, while cassette 512*a* is full, cell 500 need not be turned off.

Of importance, cassette 512*a* is within a drawer 515*a*. When cassette 512*a* is full, it can be replaced by operating personnel by opening drawer 515*a* to thereby take cassette 512*a* outside of the area protected by enclosure 513. Thus, it is unnecessary to open enclosure 513 when replacing cassette 512*a*. This also reduces the amount of time required to replace cassette 512*a*, and in particular, facilitates making it unnecessary to shut down cell 500 when replacing cassette 512*a*. (Optional cassettes 512*b* and 512*c* are similarly situated in drawers 515*b*, 515*c*, and are removed from enclosure 513 in like manner. Alarms 514*b*, 514*c* (similar to alarm 514*a*) inform the machine operator when cassettes 512*b*, 512*c* are full, but during the interval between the time cassettes 512*b*, 512*c* are full and the time they are replaced, platters that would otherwise be deposited in cassettes 512*b*, 512*c* are placed in container 508.)

Typically, at least some of the platters normally placed in cassette 512*a* are recyclable. For example, they can be re-polished and then used. Alternatively, they can be sent for further failure analysis. Although these platters may be useful, placing them into reject container 508 is not so critical that it is worth shutting down cell 500 while waiting for cassette 512*a* to be replaced, especially since a fairly small percentage of the platters would be placed in cassette 512*a*.

In one embodiment, cell 500 is controlled by a control circuit such as a microprocessor or a microcontroller (not shown).

Although cell 500 includes container 508 within enclosure 513, in another embodiment, container 508 is outside enclosure 513, and a chute (not shown) extends from inside enclosure 513 to container 508. Robotic arm 506 drops platters into the chute, and they drop into container 508. This facilitates easy and quick replacement of container 508 when it becomes full.

FIG. 17B illustrates an alternative embodiment of a cell 500' in which a cassette 516 is provided on a conveyor 518. Cassette 516 provides platters to be tested by cell 500'. If the platters pass testing, they are placed back in cassette 516. In this way, one cassette is used as both an input and output cassette. Conveyor 518 provides a steady flow of cassettes into and out of the area protected by enclosure 513.

While the invention has been described in detail, those skilled in the art will appreciate that changes can be made in form and detail without departing from the spirit and scope of the invention. For example, a head in accordance with our invention can include more or fewer optical elements than described above. Different types of optical elements can be included in the path of the incident or reflected light. Different numbers of incident light paths can be used. Also, different numbers of reflected light paths (e.g. one to six) can be used.

Although the above-described heads are made from a monolithic block of material, in other embodiments, the heads are not made from a monolithic block of material. Also, although the above-described apparatus comprises two laser sources 14, 14*d*, one for top head 12 and one for the bottom head 12*d*, in another embodiment, a single laser source can be used in conjunction with a beam splitter to provide two laser beams. Also, apparatus in accordance with the invention can be used to inspect different types of workpieces.

In one embodiment, collecting lenses 62, 72 and 77 can collimate light passing therethrough. However, in other embodiments, the light passing through these lenses need not be completely collimated. Similarly, lenses 68, 76 and 80 concentrate light. Optionally, these lenses may focus light on detectors 22-24, but this is not absolutely necessary.

One or more of the different features described above can be used without the other features described above. For example, the cylindrical lens can be used without other features described above. Accordingly, all such changes come within the invention.

We claim:

1. Apparatus comprising:
   a cylindrical lens;
   a laser source for providing a laser beam through said cylindrical lens to a workpiece, said laser beam passing repeatedly past a point on said workpiece such that the passes are displaced from the previous pass in a first direction, said laser beam illuminating a spot on said workpiece, said spot being elongated in said first direction, said cylindrical lens causing said spot to be out of focus in said first direction; and an optical detector for receiving light reflected by said workpiece, wherein the length of said spot along said first direction is substantially insensitive to the optical distance of said cylindrical lens from said workpiece.

2. Apparatus of claim 1 wherein said workpiece is disk-shaped and spins during said scanning, said laser beam moving relative to said spinning workpiece, said path extending substantially in a radial direction of said spinning workpiece.

3. Apparatus of claim 2 further comprising a second lens for focusing said laser beam onto said workpiece, said cylindrical lens reducing the effective numerical aperture of said second lens in the radial direction to thereby elongate said spot in said first direction.

4. Apparatus of claim 1 wherein said elongation facilitates more rapid inspection of said workpiece than if said spot were not elongated.

5. Apparatus of claim 1 further comprising a circuit for detecting the presence of defects in said workpiece in response to said light detected by said detector.

6. Apparatus of claim 1 wherein said workpiece is a platter.

7. Method comprising:

passing a laser beam trough a cylindrical lens:

causing said laser beam to repeatedly pass a point on a workpiece such that the passes are displaced from the previous pass in a first direction, wherein said laser strikes a spot on said workpiece, said spot being elongated in said first direction, at least some of said elongation being caused by said cylindrical lens, said cylindrical lens also causing said spot to be out of focus in said first direction; and detecting light reflected off of said workpiece with a detector, wherein the length of said spot along said first direction is substantially insensitive to the optical distance of said cylindrical lens from said workpiece.

8. Method of claim 7 wherein said workpiece is disk-shaped, said method further comprising spinning said workpiece, said first direction extending along a radial direction of said spinning workpiece.

9. Method of claim 8 further comprising passing said laser beam through a second lens that concentrates said laser beam onto said workpiece, said cylindrical lens effectively reducing the numerical aperture of said second lens in said radial direction to thereby elongate said spot in said radial direction.

10. Method of claim 7 wherein said workpiece is rotated while said laser beam traces a path in said first directiom and the elongation of said spot facilitates inspection of said workpiece more rapidly than if said spot were not elongated in said first direction.

11. Method of claim 7 further comprising detecting defects in a surface of said workpiece in response to light detected by said detector.

12. Method of claim 7 wherein said workpiece is a planer.

13. Apparatus comprising:

a first lens;

a second lens;

a light beam source providing a light beam through said first lens and then said second lens to a workpiece to thereby form a light spot on said workpiece, said first lens reducing the width of said beam along a first axis relative to a second axis perpendicular to said first axis as said beam strikes said second lens, said apparatus causing said light spot to be out of focus along said first axis, thereby elongating said light spot along said first axis, wherein the reduction of the width of said beam along said first axis as said beam strikes said second lens effectively reduces the numerical aperture of said second lens along said first axis relative to said second axis, said reduction in numerical aperture also elongating the light spot along said first axis relative to said second axis, and wherein the combination of tbe reduction of effective numerical aperture of said second lens and the causing of said light spot to be out of focus along said first axis reduces the sensitivity of the length of the light spot along said first axis to the distance between the workpiece and first lens compared to the sensitivity that would exist if the elongation of the light spot were only due to being out of focus along said first axis.

14. Apparatus of claim 13 wherein said first lens is a cylindrical lens, said cylindrical lens reducing the width of said beam along said first axis relative to said second axis as said beam strikes said second lens.

15. Apparatus of claim 13 wherein said first lens is a cylindrical lens, said second lens focuses said light spot along said second axis, and said beam is a laser beam, said apparatus further comprising an optical detector for receiving light reflected by said workpiece.

16. Method comprising:

passing a beam of light through a first lens of an optical system;

passing said beam of light through a second lens after said first lens of said optical system; and causing said beam of light to strike and form a light spot on a workpiece, said first lens reducing the width of said beam along a first axis as said beam strikes said second lens, the optical system causing said light spot to be out of focus along said first axis and thereby elongating said light spot along said first axis, wherein the reduction of the width of said beam along said first axis as said beam strikes said second lens effectively reduces the effective numerical aperture of said second lens along said first axis, said reduction in numerical aperture also elongating the light spot along said first axis, and wherein the combination of the reduction of numerical aperture of said second lens and the causing of said light spot to be out of focus along said first axis reduces the sensitivity of the length of the light spot along said first axis to the distance between the workpiece and first lens compared to the sensitivity that would exist if the elongation of the light spot were only due to being out of focus along said first axis.

17. Method of claim 16 wherein said first lens is a cylindrical lens, said cylindrical lens reducing the width of said beam along said first axis relative to a second axis perpendicular to said first axis as said beam strikes said second lens.

18. Method of claim 16 wherein said first lens is a cylindrical lens, said second lens focuses said light spot along a second axis perpendicular to said first axis, and said beam is a laser beam, said method further comprising receiving light reflected off of said workpiece with an optical detector.

* * * * *